United States Patent

Osypka

[11] Patent Number: 5,593,405
[45] Date of Patent: Jan. 14, 1997

[54] FIBER OPTIC ENDOSCOPE

[76] Inventor: Peter Osypka, Basler Str. 109, D-79639 Grenzach-Wyhlen, Germany

[21] Appl. No.: 370,034

[22] Filed: Jan. 9, 1995

Related U.S. Application Data

[63] Continuation-in-part of Ser. No. 318,312, Oct. 5, 1994, abandoned.

[30] Foreign Application Priority Data

| Jul. 16, 1994 | [DE] | Germany | 44 25 195.5 |
| Sep. 14, 1994 | [DE] | Germany | 44 32 680.7 |

[51] Int. Cl.$^6$ ............................................. A61B 17/36
[52] U.S. Cl. ............................ 606/15; 606/16; 606/7; 600/108
[58] Field of Search ............................ 606/7, 13–16, 606/27–31; 607/88, 89; 600/108

[56] References Cited

U.S. PATENT DOCUMENTS

| 4,619,247 | 10/1986 | Inoue et al. | |
| 4,699,147 | 10/1987 | Chilson et al. | 128/642 |
| 4,784,133 | 11/1988 | Mackin | 606/7 |
| 4,830,460 | 5/1989 | Goldenberg | 606/7 |
| 4,961,738 | 10/1990 | Mackin | 606/15 |
| 5,019,075 | 5/1991 | Spears et al. | 606/7 |
| 5,106,387 | 4/1992 | Kittrell et al. | 606/7 |
| 5,120,308 | 1/1992 | Hess | 604/95 |
| 5,125,925 | 6/1992 | Lundahl | 606/15 |
| 5,152,277 | 10/1992 | Honda et al. | |
| 5,279,299 | 1/1994 | Imran | 128/642 |
| 5,293,869 | 3/1994 | Edwards et al. | 128/642 |
| 5,327,889 | 7/1994 | Imran | 128/642 |
| 5,409,483 | 4/1995 | Campbell et al. | 606/13 |

FOREIGN PATENT DOCUMENTS

| 91109094 U | 12/1991 | Germany | A61B 1/00 |
| 4122909 | 1/1993 | Germany | A61M 25/01 |

*Primary Examiner*—David M. Shay
*Assistant Examiner*—Michael Peffley
*Attorney, Agent, or Firm*—Peter K. Kontler

[57] ABSTRACT

An endoscope has an elongated flexible guide the distal end of which can be introduced into a selected chamber of a human or other animal heart or into the internal space of another body organ. The tube confines a major portion of an elongated flexible sheath the distal end of which carries an inflatable balloon for the distal end portions of elongated flexible optical conductors some of which serve to illuminate selected portions of a surface bounding an internal space. The remaining conductors serve to transmit images of the illuminated portions of the surface toward the proximal end of the tube. When inflated, the ballon shields the distal ends of the conductors from contact with the body fluid in the internal space. A three-dimensional frame is provided to maintain the inflated balloon in any one of a number of different positions in a body cavity. The frame as well as the inflated balloon are constructed, assembled and dimensioned in such a way that the balloon and the frame cannot interfere with pulsating, respiratory and/or other movements of the body organ while the endoscope is in actual use.

26 Claims, 16 Drawing Sheets

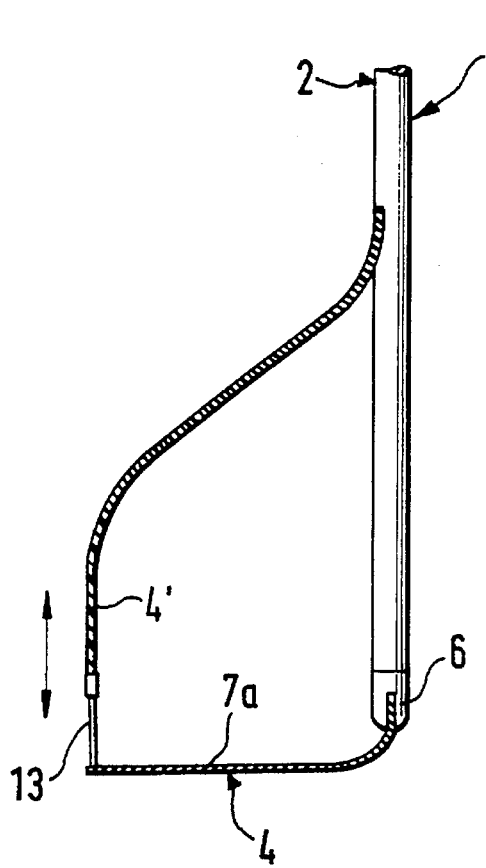
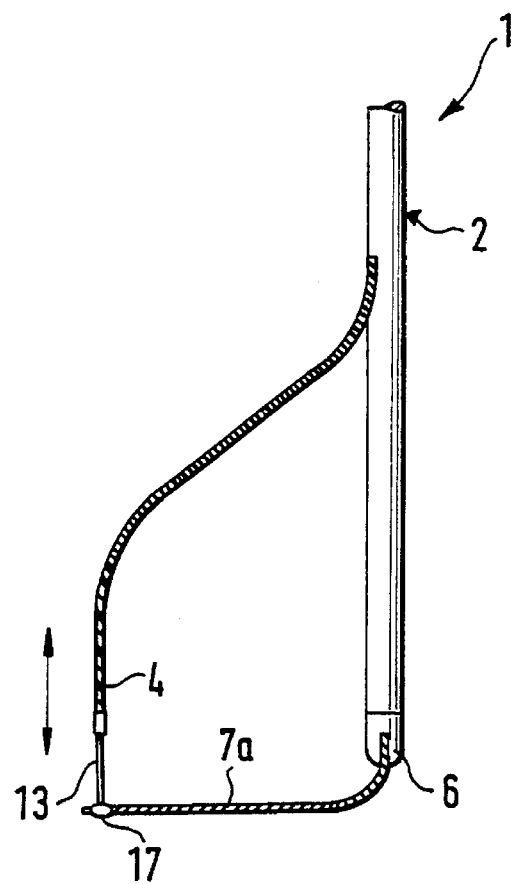
FIG.10  FIG.12
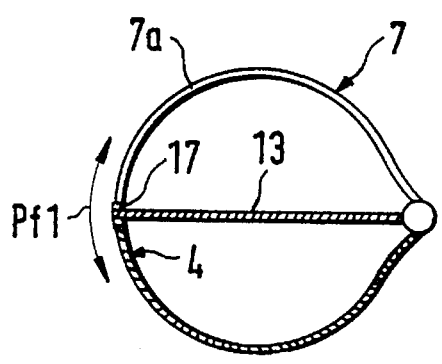
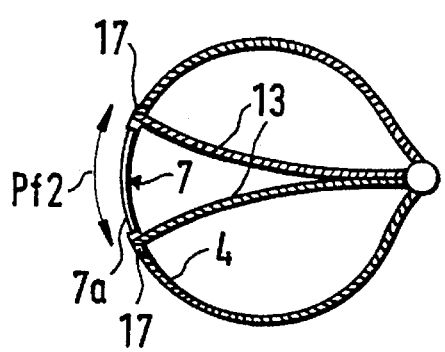
FIG.11  FIG.13

FIBER OPTIC ENDOSCOPE

CROSS-REFERENCE TO RELATED APPLICATION

This is a continuation-in-part of my patent application Ser. No. 08/318,312 filed Oct. 5, 1994 for "Mapping and ablation catheter", now abandoned.

BACKGROUND OF THE INVENTION

The invention relates to improvements in instruments which are utilized to map, ablate, illuminate and/or image the surfaces bounding the cavities or passages in body organs, such as human or other animal hearts. More particularly, the invention relates to improvements in instruments of the type known as endoscopes. An endoscope normally comprises a catheter for a set of optical conductors (e.g., glass fibers) including a first group or array of conductors which serve to direct radiation (e.g., one or more light beams) against selected portions of the surfaces bounding a chamber or passage in a body organ, and a second group or array of conductors which serve to transmit one or more images of the illuminated portions of such surfaces.

Heretofore known endoscopes which employ conductors for the transmission of radiation into and for the transmission of images from internal chambers or passages of body organs exhibit a number of drawbacks. Problems which arise when utilizing conventional endoscopes are particularly acute when the conductors are to illuminate and to transmit images of selected portions of surfaces bounding chambers in a heart or passages in conduits for body fluid (e.g., in a large conduit such as an aorta). The ability of a standard endoscope to properly illuminate and/or image selected portions of surfaces in chambers or passages of various body organs is unduly affected by the body fluid (such as blood) which flows in or through an internal chamber (e.g., a chamber of a heart), a vein or an aorta. The body fluid affects the quality (such as the brightness and sharpness) of the images.

Attempts to overcome the drawbacks of heretofore known endoscopes include the utilization of dissolved salt which is injected into the chamber or passage to be imaged, or the utilization of balloons which are to be inflated so as to expel the body fluid or fluids from that portion of an internal chamber or passage which is to be imaged with a conventional endoscope. Such proposals cannot be resorted to in connection with the imaging of a surface bounding a chamber in a human or other animal heart because the injected saline solution and/or the introduced and inflated balloon would interfere with or would actually interrupt the flow of blood through the heart. Moreover, it would be necessary to utilize an extremely large balloon to expel blood from a chamber in a human or other animal heart which, in turn, would create serious problems in connection with the introduction of a large balloon into or its extraction from a chamber in a heart. In addition, a patient would be likely to die in the course of such inspection of her, his or its heart because the heart would cease to pulsate and to circulate blood in the course of an imaging operation. In addition, the radiation issuing from certain optical conductors in a standard endoscope is likely to flicker which also affects the quality of the images. For the foregoing reasons, heretofore known endoscopes are not suitable for utilization in connection with the irradiation and imaging of surfaces in several chambers or passages of body organs or, if used, are incapable of furnishing satisfactory images or are likely to affect the condition of the patient.

OBJECTS OF THE INVENTION

An object of the invention is to provide an endoscope which is more versatile than heretofore known endoscopes.

Another object of the invention is to provide an endoscope which can complete the irradiation and imaging of selected surfaces bounding cavities, chambers and/or passages in body organs within a fraction of the time that is required to complete such operations by resorting to heretofore known endoscopes.

A further object of the invention is to provide an endoscope which can be put to use in cavities, chambers or passages of body organs without interfering, or without appreciably interfering, with the flow of body fluids through or within such cavities, chambers or passages.

An additional object of the invention is to provide an endoscope which is constructed and assembled in such a way that the quality (such as the brightness and/or sharpness and/or other parameters) of images is not affected at all, or is not appreciably affected, by the body fluid in the cavity, chamber or passage surrounded by a surface which is being illuminated and imaged.

Still another object of the invention is to provide novel and improved means for manipulating and shielding the optical conductors of the above outlined endoscope.

A further object of the invention is to provide a novel and improved endoscope which is particularly, but not exclusively, suited for the illumination and imaging of surfaces in the chambers of a human or other animal heart.

Another object of the invention is to provide novel and improved means for accurately locating and predictably shifting the distal ends of the optical conductors in the above outlined endoscope.

An additional object of the invention is to provide a novel and improved method of manipulating the above outlined endoscope.

Still another object of the invention is to provide an endoscope which, or whose constituents, can be put to use to perform numerous operations other than merely illuminating and imaging surfaces bounding cavities, chambers or passages in body organs, e.g., to carry out mapping or scanning and/or ablating operations.

A further object of the invention is to provide an endoscope which can be put to use for the imaging of surfaces surrounding the chambers of a patient's heart and which does not interfere with pulsatory movements of the heart and/or with the flow of blood.

SUMMARY OF THE INVENTION

The invention is embodied in an endoscope which comprises an elongated flexible sheath having a distal end insertable into an internal space of a body organ (e.g., into a chamber of a human or other animal heart) and a proximal end, a plurality of elongated flexible radiation- and image-transmitting conductors surrounded by and extending longitudinally of the sheath and having exposed distal ends at the distal end of the sheath to direct radiation against and to transmit images of a surface bounding the internal space of the body organ receiving the distal end of the sheath, at least one inflatable and deflatable balloon surrounding the distal ends of the conductors, and means for inflating and deflating the at least one balloon including means for establishing for the flow of a fluid into and from the at least one balloon an elongated path extending longitudinally of the sheath. The means for establishing the aforementioned path can include a lumen provided in and extending longitudinally of the sheath. The at least one balloon includes a deformable wall which is permeable to radiation (such as light) and does not interfere with the transmission of images from selected portions of an internal surface to the image-transmitting conductors. When the balloon is inflated, it is closely adjacent to a relatively small portion of the surface bounding the internal space of the body organ which is being examined so that the inflated balloon (and any other part of the improved endoscope) does not interfere with the flow of blood or another body fluid in the internal space and/or with movements of the walls surrounding the internal space (e.g., with respiratory movements and/or pulsating movements of the body organ under examination).

The improved endoscope further comprises a mechanical support or frame which includes means for urging the aforementioned portion of the deformable wall of the at least one balloon against a selected portion of the surface bounding the internal space of the body organ in the inflated condition of the at least one balloon. The means for urging can include an elongated flexible tube which surrounds the conductors at least between the proximal and distal ends of the conductors and includes a distal end at the distal ends of the conductors. The means for urging preferably further comprises at least one guide including an elongated portion or strand which is confined in the tube and a distal end portion extendable from the distal end of the tube to engage the surface bounding the internal space of the body organ adjacent the at least one balloon. The means for urging preferably further comprises means for moving the elongated portion of the at least one guide longitudinally of the tube to thus vary the size of the distal end portion of the at least one guide.

The distal end portion of the at least one guide preferably includes or constitutes a loop which can be caused to extend from the distal end of the tube to engage a selected portion of the surface bounding the internal space of the body organ being examined with the improved endoscope. The at least one guide can include at least one metallic wire and/or at least one plastic wire. The tube surrounds a portion of the sheath and the moving means can include means for shifting the at least one guide relative to the tube between a plurality of different positions (e.g., between an infinite number of different positions) to thereby select any one of a plurality of different sizes of the loop.

The endoscope preferably further comprises means for retracting the at least one balloon into and for expelling the at least one balloon from the distal end of the tube.

The at least one balloon can be provided with an internal chamber for portions of the conductors; and such conductors are preferably movable lengthwise with respect to the channel in the at least one balloon.

The aforementioned mechanical support or frame can comprise the elongated flexible tube and at least one elongated flexible guide of metallic or plastic wire. The at least one guide extends longitudinally of the sheath and includes a distal end having or constituting a loop disposed at the distal end of the sheath. Such endoscope preferably further comprises means for moving the at least one ballon and the distal ends of the conductors along the loop. Furthermore, such endoscope can comprise means for moving the guide relative to the sheath to thus vary the size of the loop. The guide can include a strand having a distal portion connected (e.g., of one piece) with the loop and being inclined relative to a plane including the loop upon completed introduction of the loop into an internal space of a body organ. The means for moving the balloon along the loop can include a tubular member having a follower tracking the loop and being movable along the loop to thereby shift the balloon along the loop. The means for moving the at least one balloon along the loop can include the aforementioned sheath or another flexible tubular member. The loop can include a first end portion which is affixed to the distal end of the elongated flexible tube, i.e., of the tube which surrounds the intermediate portion of the sheath. A second end portion of such loop is connected with the elongated strand of the guide, and such strand extends through the tube from the distal end to the proximal end of the tube. The sheath and the balloon are movable along and all the way to the first end portion of the loop.

The loop at the distal end of the flexible tube can be caused to exhibit a tendency to move into a plane making a predetermined angle (e.g., a right angle, an obtuse angle or an acute angle) with the distal end of the tube.

The loop at the distal end of the tube can be installed and configured in such a way that one of its end portions is affixed to (e.g., anchored in) the distal end of the tube and that its other end portion extends into the distal end of the tube at least substantially diametrically opposite the first end portion (with reference to a longitudinal axis of the distal end of the tube).

The at least one guide for the at least one balloon and the distal ends of the conductors can be made of a resiliently deformable wire, e.g., a plastic wire or a metallic wire, such as a wire made of NITINOL (Trademark).

The aforementioned support or frame is preferably a three-dimensional structure, and such structure can comprise a plurality of loops consisting of a resiliently deformable material. The loops can be disposed in planes which are inclined relative to each other. The three-dimensional structure can further include the aforementioned elongated flexible tube which surrounds the intermediate portion of the sheet and has a distal end adjacent to and supporting the plural loops. The distal end of the sheath, the distal ends of the conductors and the at least one balloon are preferably slidable along at least one of the loops forming part of the three-dimensional structure. Such structure can further comprise a first elongated flexible guide extending longitudinally of the tube and connected with one of the loops, and a second elongated guide extending longitudinally of the tube and connected with another loop. At least one of the guides preferably includes a portion which is confined in and is movable longitudinally of the tuber e.g., to thereby vary the size of the respective loop or to withdraw the loop into the tube during insertion of the distal end of the tube into and/or during extraction of the distal end of the tube from the internal space of a heart or another body organ.

At least one of the elongated guides can be confined in an elongated lumen provided in and extending between the proximal and distal ends of the tube. Such elongated guide, the at least one balloon and the distal ends of the conductors are preferably retractible into the tube by way of an open end of the lumen provided in or close to the distal end of the tube. The at least one balloon and the distal ends of the conductors are movable along the loop which is connected with the at least one conductor.

The novel features which are considered as characteristic of the invention are set forth in particular in the appended claims. The improved endoscope itself, however, both as to its construction and the mode of assembling and utilizing the same, together with additional features and advantages thereof, will be best understood upon perusal of the following detailed description of certain presently preferred specific embodiments with reference to the accompanying drawings.

BRIEF DESCRIPTION OF THE DRAWINGS

FIG. 10 is a fragmentary elevational view of the catheter of FIG. 6 and further shows a second conductor assembly which is used to shift the follower of the distal end portion of the second guide along the looped portion of the first guide;

FIG. 11 is a bottom plan view of the structure shown in FIG. 10;

FIG. 12 is a view similar to that of FIG. 10 but showing an additional guide which has a follower engaging the looped portion of the first guide, all as described and shown in the parent application;

FIG. 13 is a bottom plan view of the structure which is shown in FIG. 12;

DESCRIPTION OF PREFERRED EMBODIMENTS

Figure 1:
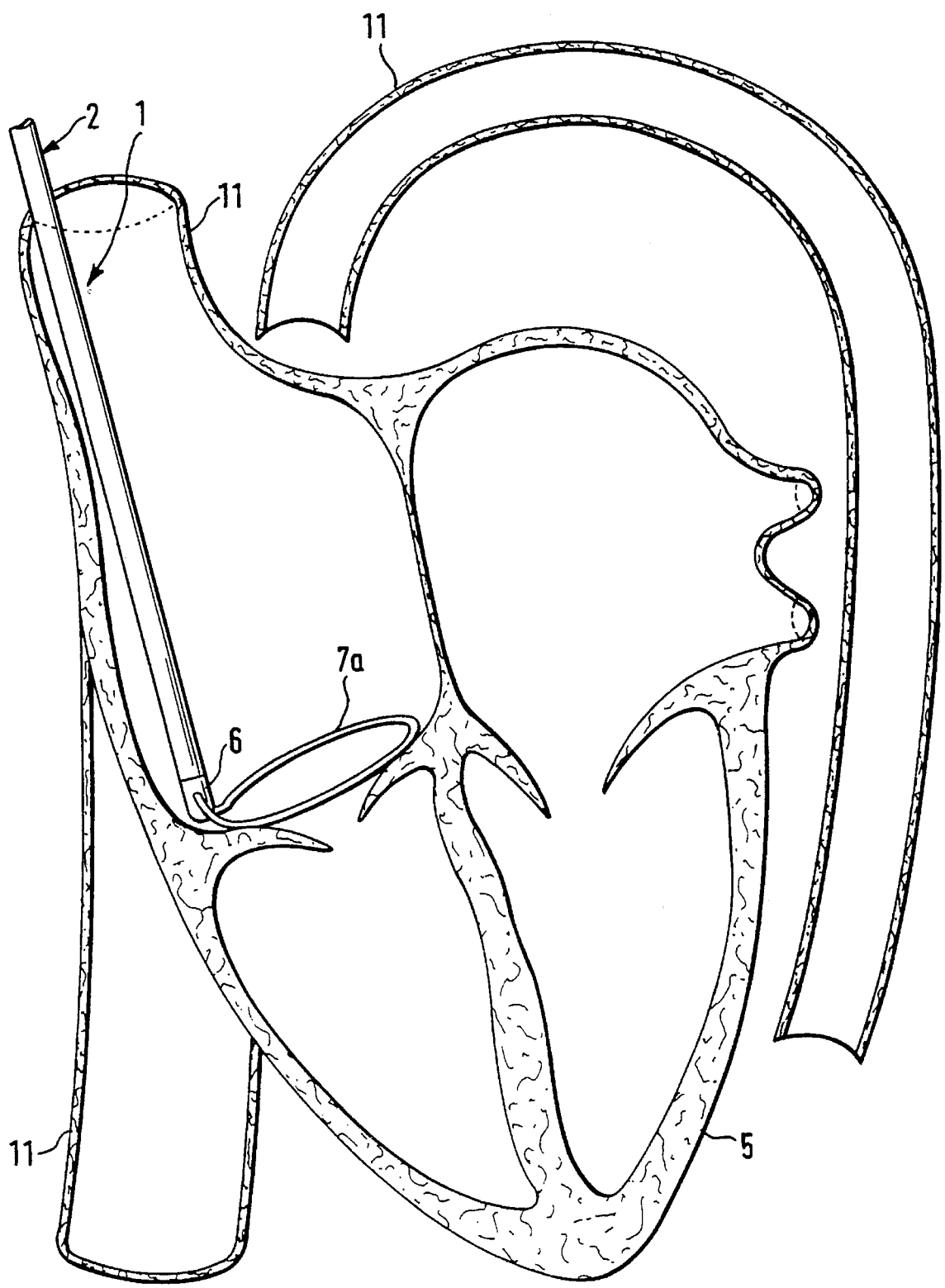
FIG. 1 is a schematic sectional view of a heart and a fragmentary elevational view of a catheter which is described and shown in the parent application and comprises a single flexible guide having a looped portion positioned in one chamber of the heart adjacent one side of a heart valve.

The following description of the mapping and ablation catheters shown in FIGS. 1 through 14 corresponds to the description of catheters shown in FIGS. 1 through 14 of the parent application.

Referring first to FIGS. 1 to 5, there is shown a catheter 1 which comprises an elongated flexible sheath 2 having distal end 6, a proximal end 2a and an elongated lumen 15 extending between the two ends 2a and 6. The catheter of FIGS. 1 to 5 further comprises an elongated flexible guide 7 having a looped portion 7a (hereinafter called loop for short) at its distal end, an elongated strand 9 in the lumen 15 and a proximal end provided with a handgrip portion or handle 10 and extending outwardly beyond the proximal end 2a of the sheath 2. The loop 7a is outwardly adjacent the distal end of the sheath 2 and includes a first end 8 anchored (at 12) in a socket 16 provided therefor in the distal end 6 of the sheath 2, and a second end which merges into the distal end of the strand 9. The handle 10 for the proximal end of the guide 7 can be manipulated relative to the handgrip portion or handle 2d on the proximal end 2a of the sheath 2 in order to move the strand relative to the lumen 15 and to thus increase or reduce the size of the loop 7a. The catheter 1 of FIGS. 1 to 5 further comprises a conductor assembly or conductor means 4 having a distal end portion 4a and a proximal end portion 4b carrying a handgrip portion or handle 4d which can be manipulated to cause the assembly 4 to slide around and along the guide 7 in a direction to move the distal end portion 4a toward and along the loop 7a (e.g., all the way or at least close to the first end 8 of the loop 7a)

or in the opposite direction. The conductor assembly 4 comprises a tube formed by a set of, for example, six or more discrete electrical conductors 3 which are convoluted to form helices surrounding the guide 7 a portion of which is received in the lumen 4c of the tube forming part of the assembly 4. The diameter of the lumen 4c at least equals and can somewhat exceed the diameter of the metallic or plastic wire which is used to make the guide 7.

Figure 4:
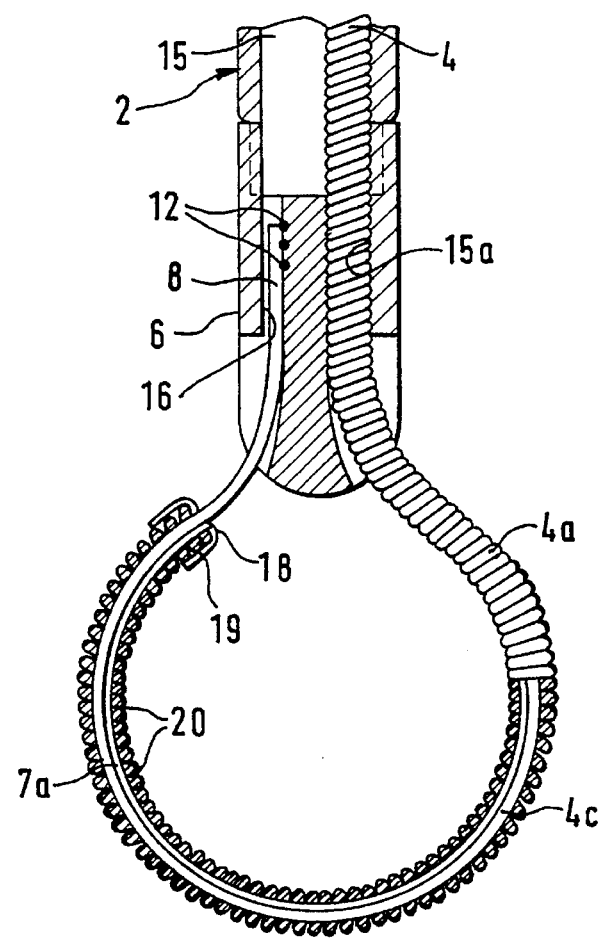
FIG. 4 is an enlarged central longitudinal sectional view of a sheath of the catheter of FIGS. 1 to 3, an elevational view of the looped portion of the flexible guide, and a partly sectional view of tubular conductor means having a lumen for the strand and for the looped portion of the flexible guide.

FIG. 4 shows that the lumen of the sheath 2 has an outlet 15a in the distal end 6 and that the diameter of the outlet 15a suffices to ensure that the assembly 4 can be caused to move its distal end portion 4a through such outlet on its way toward or away from the first end 8 of the loop 7a. The helices of conductors 3 forming part of the assembly 4 are insulated from each other all the way from the proximal end portion 4b to the distal end portion 4a but the distal end portions of the conductors 3 are bare at selected locations of the distal end portion 4a to constitute terminals or poles (such as 18 or 20) which can be used to map selected portions of a heart 5, e.g., to map or scan one side of a valve between two chambers of the heart which is shown schematically in FIG. 1 of the drawings.

The poles or terminals 20 can be formed by removing insulation from the conductors 3 at the distal end portion 4a of the assembly 4. Such terminals remain insulated from each other but can be caused to contact selected portions in the interior of the heart 5 or in another body organ. The insulation is removed from relatively small (such as punctate or punctiform) portions of the conductors 3. The conductor assembly 4 can be utilized for point-by-point mapping or scanning of the internal surface of the heart 5 and/or for transmission of cardiac signals and/or for determination of electrical potentials in a patient's heart. Furthermore, the catheter 1 can be used with equal or similar advantage for cardiac surgery, e.g., to ablate selected parts of afflicted tissue. Still further, the catheter 1 can be utilized as an instrument which applies to the heart suitable stimulating impulses. FIG. 1 shows that the distal end of the sheath 2 has been introduced into a cardiac chamber through the most convenient blood vessel 11 so that the exposed loop 7a of the guide 7 lies against the adjacent side of a heart valve.

Figure 6:
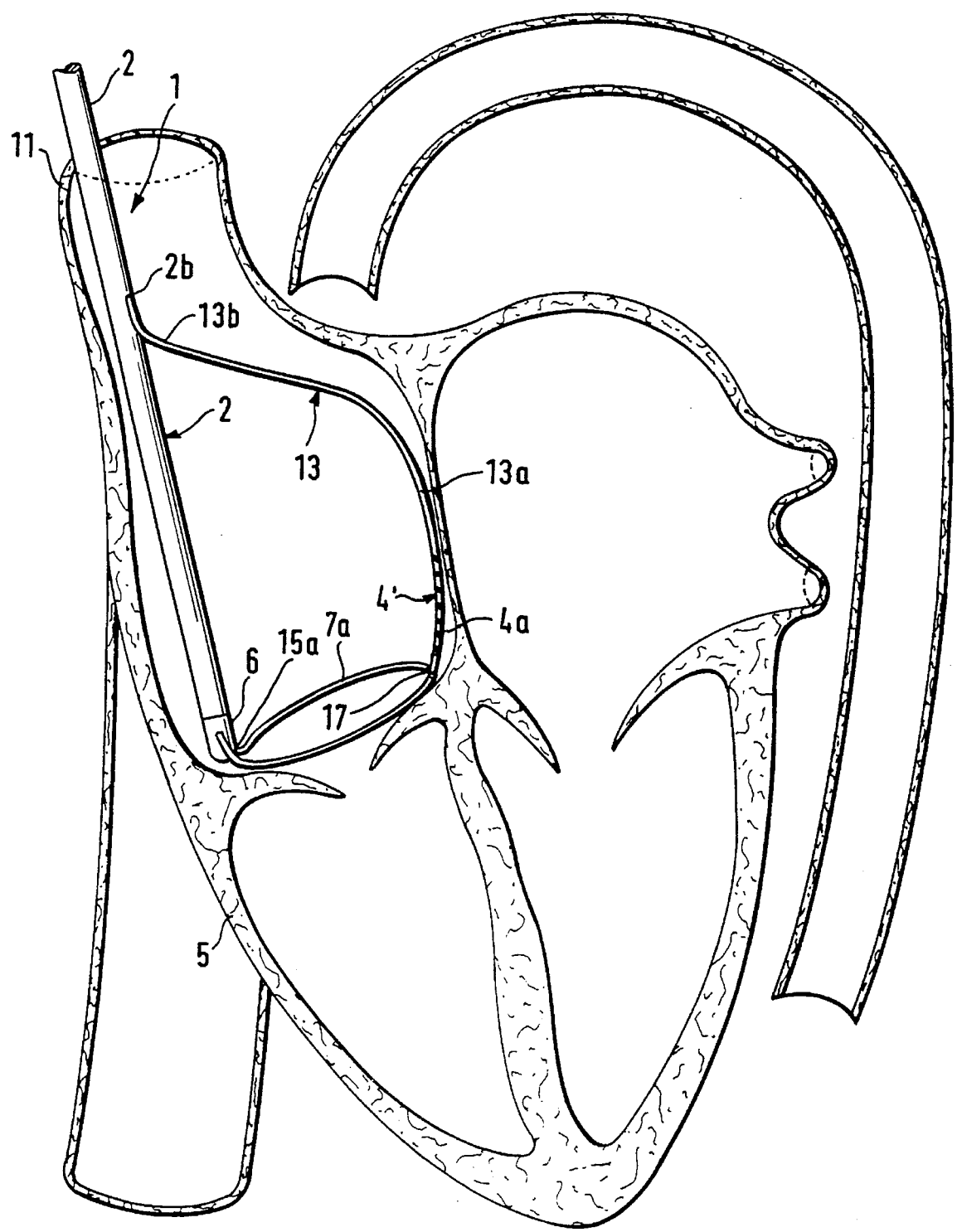
FIG. 6 is a view similar to that of FIG. 1 but showing a portion of a modified catheter which is also disclosed in the parent application and comprises two flexible guides.

The metallic or plastic wire which is used to make the guide 7 is resilient, i.e., it can reassume and tends to reassume a predetermined shape or orientation. Furthermore, the guide 7 includes a resiliently deformable section or portion 14 (FIG. 2) which causes the loop 7a to dwell in a predetermined plane until and unless the loop 7a is caused to move into a different plane, e.g., as a result of moving the loop against an internal surface in a body organ or due to the action of one or more additional guides such as a guide 13 which is shown in FIG. 6. The loop 7a of FIG. 4 is located in a plane which makes with the distal end 6 of the sheath 2 a relatively large obtuse angle, e.g., an angle close to 135°.

Figure 5:
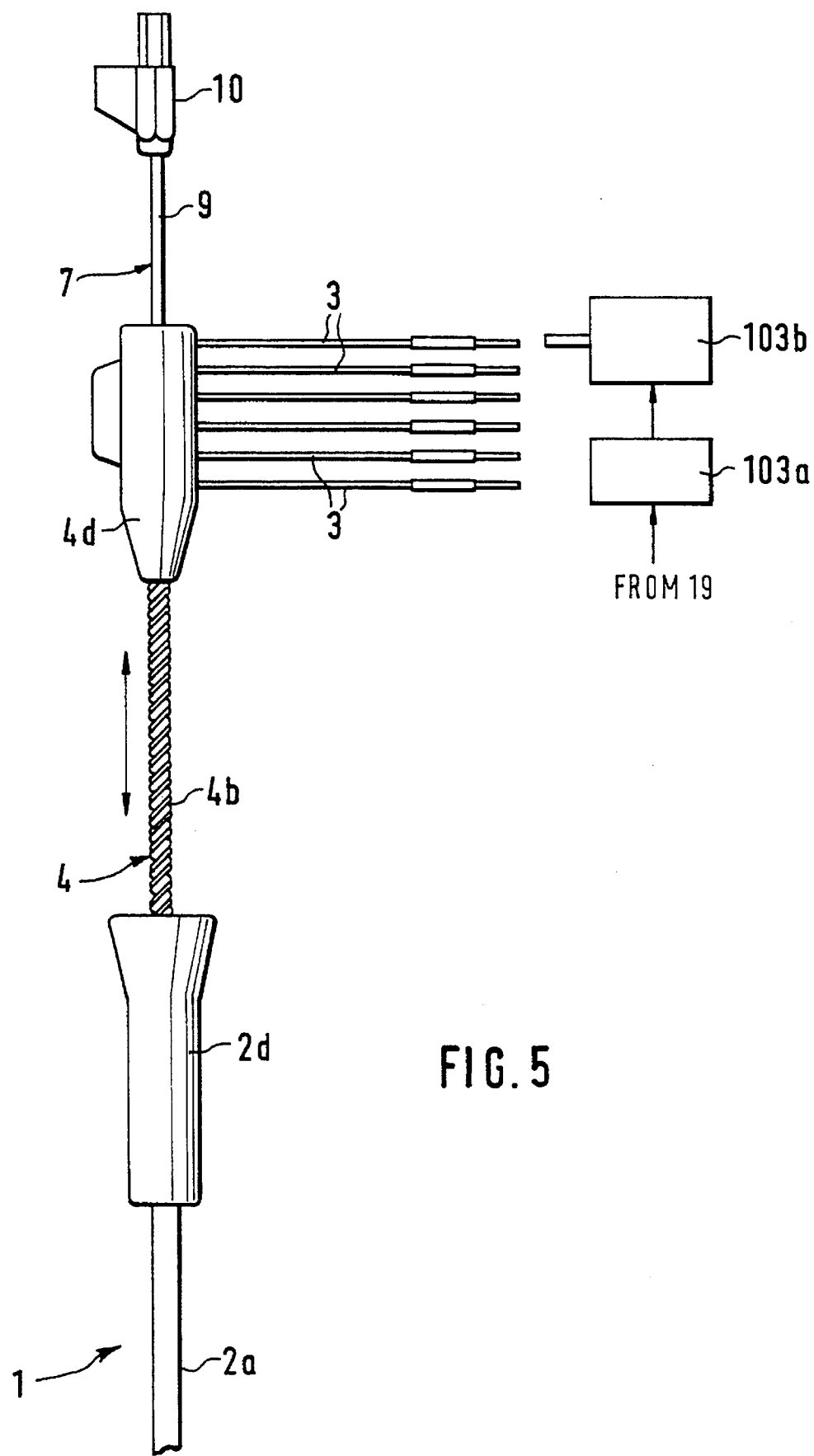
FIG. 5 is an enlarged partly elevational and partly diagrammatic view of the structure at the proximal end of the sheath forming part of the catheter shown in FIGS. 1 to 4.

The handle or handgrip member 10 of FIG. 5 can be manipulated to move the strand 9 of the guide 7 between an infinite number of different positions relative to the sheath 2, i.e., the size of the loop 7a can be varied infinitely to thus ensure that the terminals of the conductors 3 can be moved to optimal positions relative to a selected internal surface of the heart 5 or another body organ.

The guide 7 of the catheter 1 shown in FIGS. 1 to 5 can be utilized as a means for steering the distal end portion 4a of the conductor assembly 4 to a predetermined position in a body organ and for maintaining the terminals of the conductors 3 in desired positions for the purposes of mapping, ablating or stimulating. However, the guide 7 can also serve as a means for steering to one or more desired positions the terminals of a conductor assembly (such as the conductor assembly 4 or a second conductor assembly 4' shown in FIG. 6). One of two conductor assemblies (such as 4 and 4') can be used to shift the distal end portion of the other conductor assembly relative to the loop 7a of the guide 7.

By retracting the handle 10 for the proximal end of the strand 9 to a position at a maximum distance from the handle 2d for the proximal end 2a of the sheath 2, the person in charge can reduce the size of the loop 7a to a minimum value. Thus, and if the distal end portion 4a of the conductor assembly 4 is withdrawn into the lumen 15 of the sheath 2 prior to a reduction of the size of the loop 7a to a minimum value, the still exposed portion of the wire or strand forming the guide 7 merely extends from the open end of the socket 16, along the rounded tip of the distal end 6 of the sheath 2, and into the outlet 15a of the lumen 15. This enables the person in charge to introduce the distal end or leader 6 of the sheath 2 into a selected blood vessel 11 and into a selected chamber of the heart 5 or another internal body organ. In other words, neither the guide 7 nor the conductor assembly 4 can interfere with rapid and trauma-free introduction of the distal end 6 of the sheath 2 into a selected portion of a body organ. However, once the distal end 6 has been advanced to a desired position, e.g., in a chamber of the heart 5, the person in charge can manipulate the handle 10 to increase the size of the loop 7a to any desired value in order to establish a path for the advancement of the terminals 20 at the distal end portion 4a of the assembly 4 to desired positions in the selected chamber of the heart. FIG. 1 shows that the size of the loop 7a is selected with a view to ensure that the distal end portion 4a of the assembly 4 can be advanced along the loop 7a to any one of a practically infinite number of different positions relative to the adjacent side of the left-hand valve in the heart 5 of FIG. 1. All that is necessary is to manipulate the handle 4d in order to move the distal end portion 4a of the conductor assembly 4 along the loop 7a, either toward the socket 16 or in a direction from the socket 16 toward the outlet 15a of the lumen 15. The material of the loop 7a is sufficiently flexible to ensure that it can readily follow the outline of a selected internal surface of a body organ. This, in turn, ensures that the terminals 20 of the conductors 3 forming part of the assembly 4 can be moved sufficiently close to selected parts of the internal surface of an organ in order to guarantee satisfactory transmission of signals from such selected parts to one or more instruments which are connected to the proximal ends of the conductors 3 or to guarantee predictable transmission of stimuli or other signals to the selected parts of the internal surface.

FIG. 4 shows that the loop 7a can form a circle which renders it possible to advance the terminals 20 of the conductors 3 along an arc of close to 360°. The handle 4d on the proximal end portion 4b of the assembly 4 can be moved relative to the handles 2d and 10 in stepwise fashion so that the distal end portion 4a of the assembly 4 can map or scan, point-by-point, the selected portion of a surface in the heart 5 or another internal organ. For example, the person in charge will advance the distal end portion 4a of the assembly 4 all the way to the end 8 of the loop 7a to thereupon retract the distal end portion 4a into the lumen 15 in a stepwise fashion so that the terminals 20 can map a selected part of an internal surface of the heart 5 of FIG. 1 with a requisite degree of accuracy. At such time, the loop 7a ensures that the terminals 20 advance along a predetermined or preselected path. The mapping operation can be repeated as often as necessary, either along the previously mapped portion of the internal surface or along successively selected different portions of such internal surface.

The position of the loop 7a relative to the internal surface in the upper left-hand chamber of the heart 5 which is shown in FIG. 1 can be changed by merely shifting the distal end 6 of the sheath 2 by way of the handle 2d or subsequent to a reduction of the size of the loop 7a (with the handle 10) and, if necessary, subsequent to partial or complete retraction of the distal end portion 4a of the assembly 4 into the lumen 15.

The construction of the conductor assembly 4' which is shown in FIG. 6 is or can be identical with that of the conductor assembly 4. Thus, the conductor assemblies 4 and 4' can be used interchangeably to advance their distal end portions 4a, 4a' along the loop 7a or to advance their distal end portions 4a, 4a' along that portion of a guide 13 which extends from a second outlet 2b of the sheath 2. The outlet 2b is adjacent to but spaced apart from the outlet 15a so that a variable length of the strand 13b forming part of the guide 13 can extend between the distal end portion 4a' of the conductor assembly 4' and the outlet 2b. The exposed portion of the strand 13b can be used as a means for propping the loop 7a against movement relative to a selected portion of the internal surface of the heart 5. The strand 13b (and more specifically that portion of the assembly 4' which surrounds the exposed length of the strand 13b) can engage the internal surface in the respective chamber of the heart 5 at a desired distance from the locus where a follower 17 (e.g., a hook or an eyelet) at the distal end 13a of the guide 13 slidably engages the loop 7a.

The helical convolutions of the conductor assembly 4 or 4' can constitute separately produced insulated wire-like components having proximal ends electrically connected to the conductors 3 shown in FIG. 5 and partially bare distal ends to form the terminals or poles 20. As already mentioned before, the diameter of the lumen defined by the tube which forms part of the conductor assembly 4 is sufficiently large to ensure that the wire-like material of the guide 7 can be slidably received therein. It is presently preferred to select the diameter of the lumen 4c in such a way that it can also slidably receive the wire of the guide 13. Analogously, the diameter of the lumen defined by the conductor assembly 4' is or can be selected in such a way that the lumen of the assembly 4' can slidably receive the wire of the guide 7 or the wire of the guide 13. This contributes to the versatility of the catheter. FIG. 4 shows, by way of example, that the diameter of the lumen 4c defined by the conductor assembly 4 exceeds the diameter of the wire which is used to make the guide 7.

Figure 2:
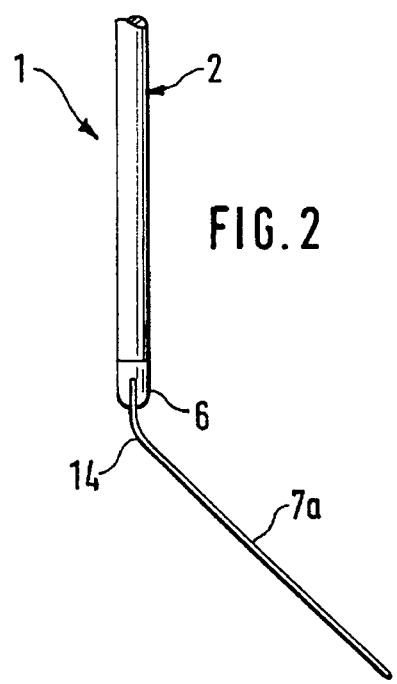
FIG. 2 is a side elevational view of that portion of the catheter which is shown in FIG. 1 but prior to insertion into or subsequent to extraction from the heart chamber.
Figure 3:
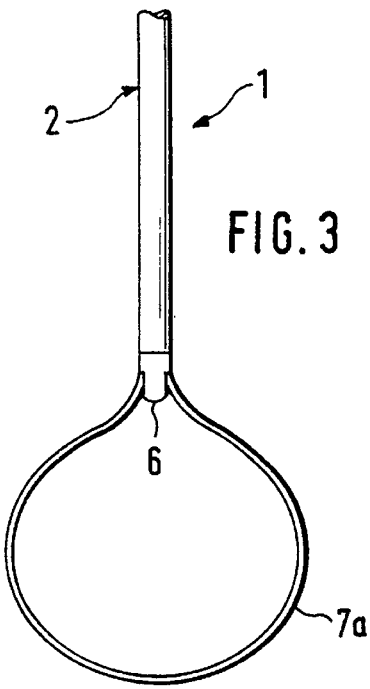
FIG. 3 is a view of the catheter portion as seen in a direction from the right or from the left in FIG. 2.

The guide 13 may but need not always be provided with a section of the type shown at 14 in FIG. 2. The section 14 receives the desired shape in the manufacturing plant so that it continuously exhibits the tendency to maintain the loop 7a in a plane making a desired angle with the distal end 6 of the sheath 2. The section 14 can be readily deformed in response to retraction of the loop 7a into the lumen 15 but is again ready to position the loop 7a in a predetermined plane (relative to the distal end 6) as soon as a portion of or the entire loop 7a shown in FIGS. 2 and 3 is expelled from the lumen 15 of the sheath 2. Once the leader or distal end 6 of the sheath 2 is introduced into a selected chamber of the heart 5, adequate positioning of the loop 7a relative to the adjacent internal surface or surfaces of the heart does not necessitate any further shifting of the distal end 6, i.e., the person in charge manipulates the handle 10 to select the size of the loop 7a and, once the loop properly engages the adjacent internal surface or surfaces, it performs the additional function of maintaining the distal end 6 in a requisite position. The next step involves the manipulation of the handle 4d in order to move the terminals 20 of the distal end portion 4a to requisite positions relative to the adjacent internal surface or surfaces. As can be seen in FIG. 1, the provision of the arcuate section 14 ensures that the loop 7a can extend laterally of the distal end 6 and that the distal end 6 is located at one side of the left-hand valve in the heart 5.

The first end 8 of the loop 7a can be affixed to the distal end 6 of the sheath 2 in a manner other than that shown in FIG. 4. However, the placing of the socket 16 substantially diametrically opposite the outlet 15a of the lumen 15 is preferred in many or most instances because this reduces the likelihood of excessive deformation of the wire forming the guide 7 when the size of the loop 7a is reduced to a minimum value.

The diameter of the lumen 15 in the sheath 2 is sufficiently large to ensure that the sheath can confine the strand 9 of the guide 7 as well as the strand 13b (FIG. 6) of the guide 13. However, it is also possible to provide the sheath 2 with two or more lumina, e.g., a discrete lumen for each of a plurality of guides (such as the guides 7, 13 and one or more additional guides, e.g., a guide 7' shown in FIG. 8).

The loop 7a of the guide 7 and the exposed distal end 13a of the guide 13 shown in FIG. 6 together constitute a three-dimensional guide assembly for a single conductor assembly 4 or 4' or for the conductor assemblies 4 and 4'. As can be seen in FIG. 6, the distal end portion 4a' of the conductor assembly 4' can be moved along the exposed distal end portion 13a to ensure that the terminals of conductors forming part of the assembly 4' can be moved to requisite positions relative to the adjacent portion of the internal surface of the heart 5. The conductor assembly 4 (not shown in FIG. 6 for the sake of clarity) can be used to shift the follower 17 at the tip of the distal end or end portion 13a of the guide 13 along the loop 7a, i.e., to establish a different path for the movement of the distal end portion 4a' along the internal surface in the respective chamber of the heart 5. In lieu of the conductor assembly 4, the catheter of FIG. 6 can be furnished with a flexible hose or another tubular member (not shown) which can be slipped onto the guide 7 to move the follower 17 along the loop 7a of the guide 7. For example, the conductor assembly 4 or 4' can be used to move its distal end portion 4a or 4a' along the distal end portion 13a of the guide 13 or along the loop 7a of the guide 7, and a discrete tubular moving device can be used to shift the follower 17 along the loop 7a.

An advantage of the three-dimensional framework including the guides 7 and 13 of FIG. 6 is that the loop 7a and/or the distal end portion 13a can be even more reliably maintained in a desired or optimum position prior to advancement of the distal end portion 4a or 4a' along the distal end portion 13a or along the loop 7a. Such reliable positioning of the distal end portion 13a and of the loop 7a further ensures that the conductor assembly 4 and/or 4' can be used for accurate point-by-point mapping or scanning of the internal surface of a body organ.

The follower 17 of the distal end portion 13a of the guide 13 can constitute a hook, an eyelet or a relatively short sleeve having a passage which can receive the adjacent portion of and can be readily shifted along the loop 7a of the guide 7.

The catheter 1 can further serve as an ablation catheter. This can be achieved by providing the conductor assembly 4 and/or 4' with a terminal (note the terminal 18 in FIG. 4)

which is connectable to a suitable source (103 in FIG. 5) of high-frequency energy. It is also possible to connect a plurality of conductors 3 of the assembly 4 or 4' with a source of high-frequency energy. The terminal or terminals 18 can be provided in addition to the terminal(s) 20 of the respective conductor(s) 3. FIG. 4 further shows a temperature sensor 19 which is carried by the distal end portion 4a of the conductor assembly 4 adjacent the terminal 18. It is also possible to install the temperature sensor 19 in the terminal 18. Signals from the temperature sensor 19 are or can be utilized to regulate the transmission of energy from the source 103 to the terminal 18. The temperature sensor 19 is connected to the regulating means 103a for the application of energy to the terminal 18 by one or more conductors in the lumen 4c of the distal end portion 4a of the conductor assembly 4.

The conductor assembly 4' can also comprise one or more terminals 18 connectable to the energy source 103 or to a separate source.

As already mentioned hereinbefore, the guide 7 and/or the guide or guides 13 and/or the guide 7' can be made of a metallic or plastic wire. It is presently preferred to employ a metallic wire, e.g., a wire made of NITINOL (Trademark). Such wire exhibits a highly satisfactory pronounced flexibility, pronounced resistance to buckling and the ability to repeatedly reassume a preselected shape even if its diameter is small or very small. Wire made of NITINOL can be obtained from NITINOL Development Corp., 48501 Warm Springs Blvd., Fremont, Calif. It is also possible to employ a wire made of TINEL (Trademark) which can be obtained from Raychem Corp., 300 Constitution Drive, Menlo Park, Calif.

Experiments indicate that a guide made of or containing NITINOL or TINEL can be caused to readily assume a desired shape, e.g., a loop 7a or 7a' (FIG. 8) made of such material can closely follow the outline of the surface bounding a chamber in the heart 5 in response to the application of relatively small forces to thus ensure atraumatic introduction into a body organ. However, once the application of force or forces to a loop made of NITINOL or TINEL is terminated, the loop automatically reassumes a preselected shape and moves into a plane making a selected angle with the distal end 6 of the sheath 2. A guide exhibiting the aforementioned desirable characteristics can be used to properly follow the outline of a surface in a heart and/or another body organ.

Figure 7:
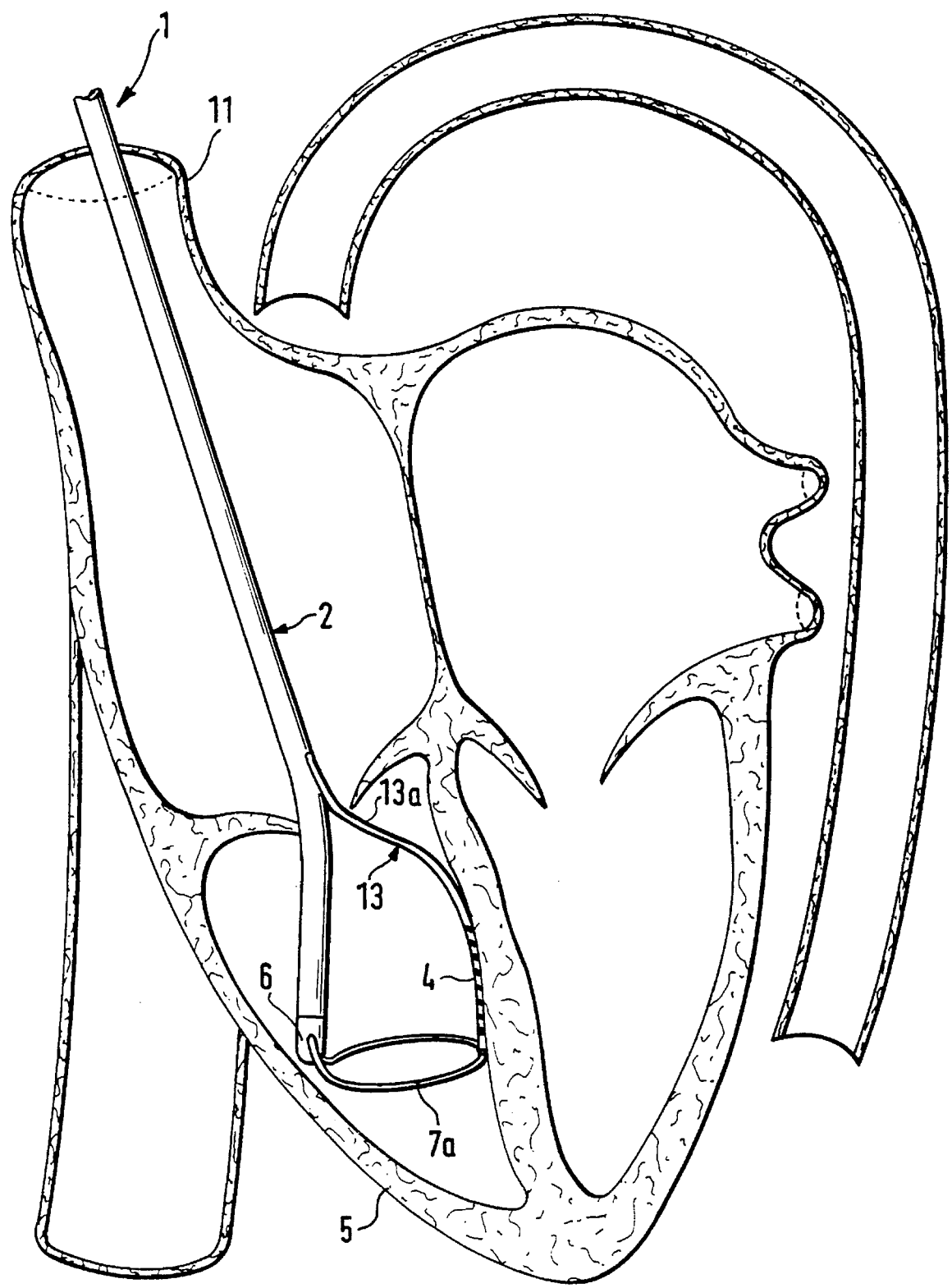
FIG. 7 is a view similar to that of FIG. 6 but showing a catheter (also described and shown in the parent application) with two flexible guides in another chamber of the heart.

The position of the loop 7a of the guide 7 which is shown in FIG. 1 is the same as that of the loop 7a shown in FIG. 6 but the loop 7a of FIG. 6 forms part of the aforementioned three-dimensional guide assembly because the catheter of FIG. 6 employs the guide 7 as well as the guide 13. FIG. 7 shows the catheter 1 of FIG. 6 but with the loop 7a and the distal end portion 13a of the guide 13 located in another internal chamber of the heart 5.

Figure 8:
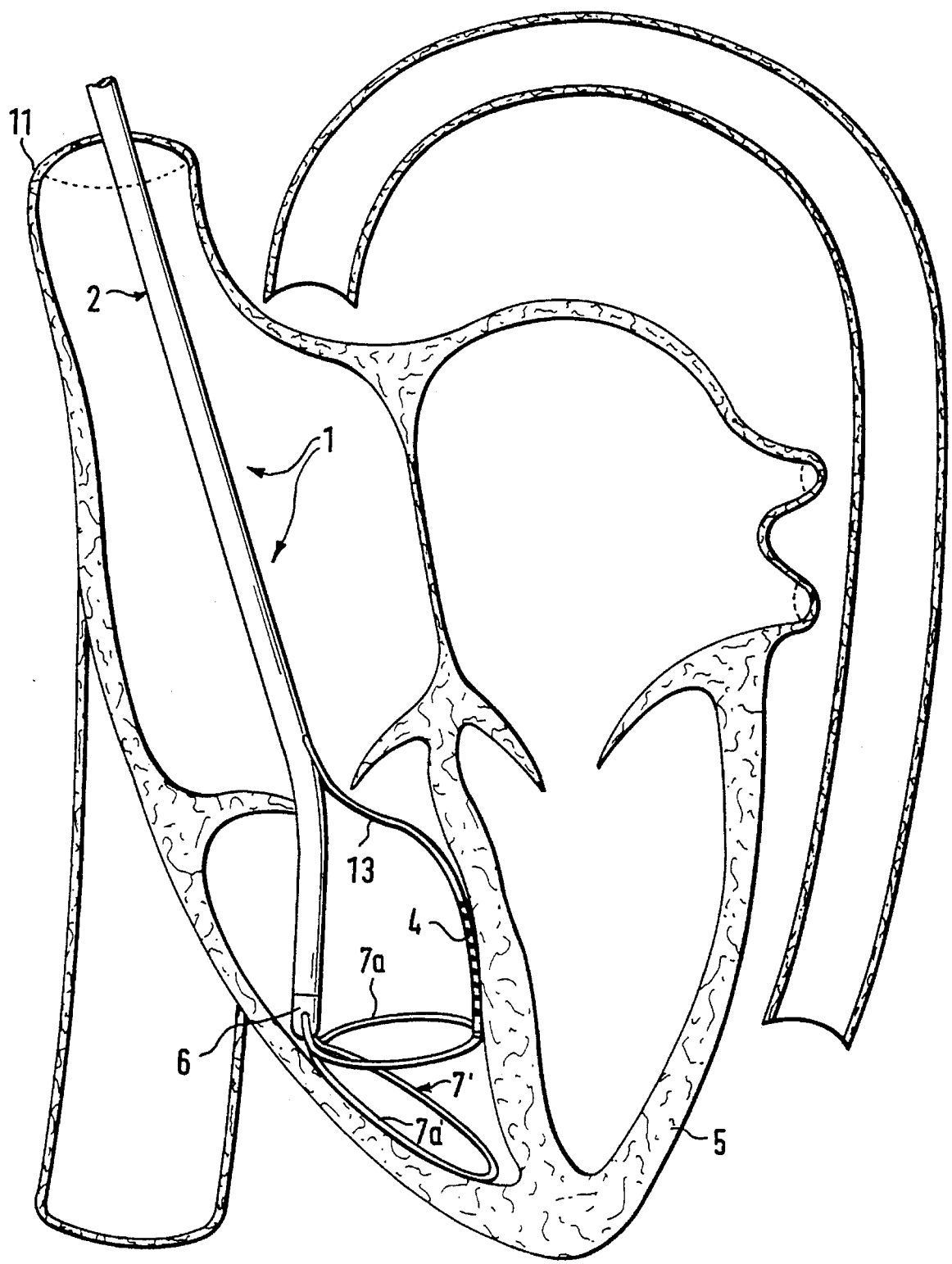
FIG. 8 is a view similar to that of FIG. 1, 6 or 7 but showing a portion of a third catheter (also disclosed in the parent application) which employs the flexible guides of FIG. 7 and a further flexible guide.

FIG. 8 shows the structure of FIG. 7 and the guide 7' which is or which can be identical with the guide 7 except that, in the absence of any stresses, its loop 7a' is located in a plane other than the plane of the loop 7a. The inclination of the plane for the loop 7a' relative to the distal end 6 of the sheath 2 is greater than that of the plane for the loop 7a. Thus, the follower of the distal end portion of the guide 13 is movable along the loop (7a) located in a plane making with the distal end 6 an angle which is smaller than the angle between the distal end 6 and the plane for the other loop (7a'). The catheter 1 of FIG. 8 can employ a first conductor assembly 4' which can be caused to move along the distal end portion of the guide 13, a second conductor assembly (corresponding to the assembly 4 shown in FIGS. 4, 5 and 7) and a third conductor assembly (not shown) which can be identical with or similar to the assembly 4 or 4' and can be caused to move its distal end portion along the loop 7a'. A single conductor assembly can be utilized to move its distal end portion along the distal end portion of the guide 13 or along the loop 7a or along the loop 7a'.

An advantage of the catheter 1 which is shown in FIG. 8 is that the three-dimensional frame assembly including the the guides 7, 7' and 13 renders it possible to even more reliably position the loop 7a, the loop 7a' and the distal end portion of the guide 13 relative to the adjacent portions of the surface bounding the respective chamber of the heart 5 or another internal body organ. Thus, the loop 7a extends along a first portion, the loop 7a' extends along a second portion, and the distal end portion of the guide 13 extends along a third portion of the surface bounding the cardiac chamber which receives the distal end 6 of the sheath 2. This renders it possible to carry out point-by-point mapping of the internal surface along the loop 7a and/or 7a' and/or along the distal end portion of the guide 13 with an even higher degree of accuracy.

The catheter 1 of FIG. 8 can be utilized with particular advantage for mapping an internal surface close to the lowermost part of the heart 5. The frame assembly including the guides 7, 7' and 13 is sufficiently stable to establish preselected paths for the distal end portion of the conductor assembly 4 or 4' or an additional conductor assembly while being sufficiently flexible to ensure unimpeded pulsation of the heart. The strands of the guides 7, 7' and 13 can be confined in a common lumen (such as the lumen 15 shown in FIG. 4) or the sheath 2 of the catheter 1 shown in FIG. 8 can be provided with a plurality of lumina, e.g., one for each of the three strands.

FIG. 8 further shows that the second ends of the loops 7a and 7a' extend into a common outlet of the distal end 6 (such as the outlet 15a shown in FIG. 4) and that the first ends of such loops are anchored in the distal end 6 at a locus disposed at least substantially diametrically opposite the outlet. Though the distal end 6 can be provided with a discrete outlet for each of the guides 7 and 7', the utilization of a single outlet (as shown in FIG. 8) is normally preferred because the two loops 7a and 7a' extend in the same direction (but in different planes) relative to the distal end 6. Such selection of the direction in which the loops 7a and 7a' extend from the distal end 6 has been found to contribute to more reliable positioning of the loops 7a and 7a' as well as of the distal end portion of the guide 13 in a selected chamber of the heart 5 or in a selected chamber (or a single chamber) of another body organ. The loops 7a, 7a' and the distal end portion of the guide 13 cooperate to maintain the distal end 6 of the sheath 2 in a selected position with reference to the wall bounding the respective internal chamber.

The catheter 1 of FIG. 8 can be simplified by omitting the guide 13, i.e., by utilizing only the two loops 7a and 7a' as a means for properly positioning the distal end of the catheter in an internal chamber or passage. However, the utilization of the guides 7 and 7' in combination with the guide 13 is normally preferred because it enhances the versatility of the catheter by establishing a number of additional paths for the movement of the distal end portion of a conductor assembly along the distal end portion of the guide 13. The latter preferably includes a follower (not specifically shown in FIG. 8) which can resemble the follower 17 in FIG. 6 so that the distal end portion of the guide 13 can be shifted longitudinally of the loop 7a to establish a practically infinite number of paths for the mapping in directions from the left-hand valve of the heart 5 shown in FIG. 8 toward the selected portion of the loop 7a.

Figure 9:
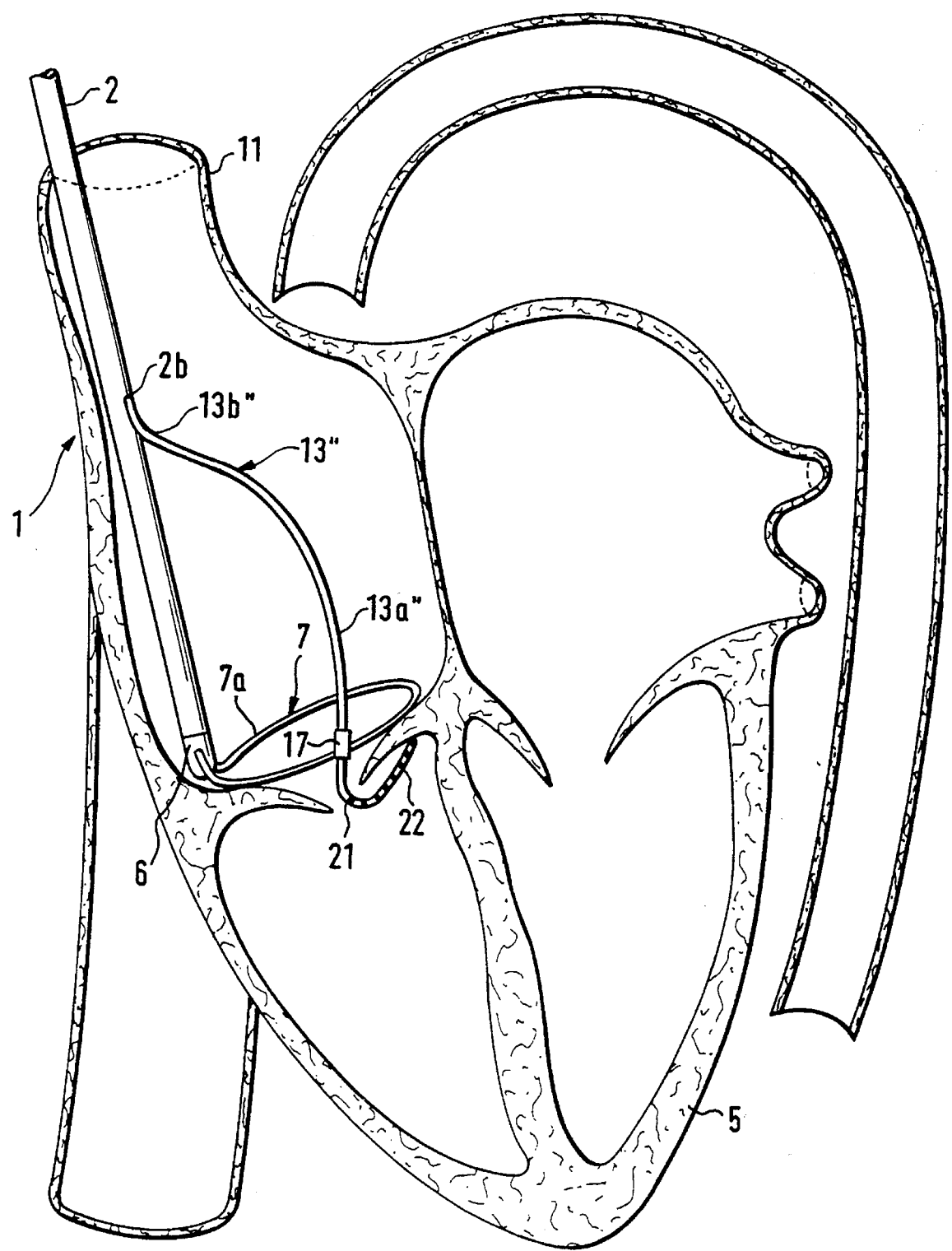
FIG. 9 is a view similar to that of FIG. 1, 6, 7 or 8 but showing a modified conductor assembly in the process of mapping one side of a heart valve, all as described and shown in the parent application.

FIG. 9 illustrates a further catheter 1 utilizing a first guide 7 having a loop 7a and a hollow tubular flexible guide 13" having a distal end portion 13a' provided with a follower 17 slidable along the loop 7a. The elongated median portion 13b" of the guide 13" extends from the lumen of the sheath 2 through the outlet 2b and merges into the distal end portion 13a'. The guide 13" has a lumen for a conductor assembly 21 which is slidable in such lumen and includes a substantially J-shaped distal end portion 22. The loop 7a is located at one side of the left-hand valve in the heart 5 of FIG. 9 and the distal end portion 22 of the assembly 21 extends through the opening in and toward the other side of such valve. Thus, the catheter 1 of FIG. 9 can be utilized for point-by-point mapping of one side of the valve by the distal end portion of a conductor assembly corresponding to the assembly 4 or 4', and for point-by-point mapping of the other side of the valve by the terminals (not specifically shown) which are provided at the distal end portion 22 of the assembly 21. Furthermore, the J-shaped distal end portion 2 of the conductor assembly 21 cooperates with the adjacent portion of the heart valve to reduce the likelihood of undesirable shifting of the loop 7a relative to the respective side of the valve. A conductor assembly (such as 4 or 4') or a hose-like implement can be utilized to move the follower 17 of the tubular guide 13" along the loop 7a and to thus change the position of the distal end portion 22 of the assembly 21 relative to the underside of the left-hand valve in the heart 5 of FIG. 9.

The conductor assembly 21 of FIG. 9 can comprise one or more insulated conductors. The guide 13" can be said to constitute a second catheter which can be utilized in or with the catheter utilizing the sheath 2 and the guide 7 of FIG. 9. The follower 17 can be moved along the loop 7a by a conductor assembly 4 or 4' or by an implement resembling the tubular guide 13".

An advantage of the catheter 1 which is shown in FIG. 9 is that it facilitates convenient, rapid and accurate mapping of that side of a heart valve (namely a side corresponding to the underside of the left-hand valve shown in FIG. 9) which cannot be readily mapped with heretofore known catheters. The conductor assembly 21 of FIG. 9 can be utilized for mapping or as an ablation instrument for surgical removal of tissue at the hard-to-reach side of a heart valve. If the assembly 21 is used as an ablation instrument, its distal end portion 22 is held in one or more selected positions by the loop 7a at the more readily accessible side of the heart valve. As mentioned above, a conductor assembly 4 or 4' (or a moving implement resembling the tubular guide 13") can be used to shift the follower 17 along the loop 7a to thereby advance the J-shaped distal end portion 22 of the assembly 21 to any one of a practically infinite number of different positions.

FIGS. 10 and 11 illustrate the catheter 1 of FIG. 2 or 3, a conductor assembly 4 having a distal end portion movable along the loop 7a of the guide 7, and a conductor assembly 4' (which may be identical with the assembly 4) having a distal end portion movable along the guide 13. The distal end portion of the assembly 4 is movable along the loop 7a (in the directions indicated by a double-headed arrow Pf1) for the purpose of mapping, ablation, impulse transmission or impulse reception. In addition, the distal end portion of the assembly 4 is or can be used as a means for moving the follower 17 along the loop 7a. If the distal end portion of the assembly 4 is coupled to the follower 17, such distal end portion can move the follower in each of the two directions indicated by the double-headed arrow Pf1.

The conductor assembly or assemblies (e.g., the conductor assembly 4 or 4') preferably constitutes or constitute multicoil arrangements. The coil or coils are sufficiently stiff to push or pull the corresponding follower (such as the follower 17 shown in FIG. 11) in both directions along the respective guide. For example, the left-hand end of the conductor assembly 4 shown in FIG. 11 can be affixed to the follower 17 so that the latter can be moved in the directions indicated by the arrow Pf1 in response to corresponding movements of the conductor assembly 4.

FIGS. 12 and 13 illustrate a portion of a catheter 1 which includes the sheath 2, the guide 7, and two guides 13 each having a follower 17 movable along the loop 7a of the guide 7. Each of the two followers 17 is movable in at least one of the two directions indicated by a double-headed arrow Pf2 by the distal end portion of a conductor assembly 4. The two followers 17 can be held at a selected distance from each other by a distancing element (e.g., a sleeve) which is slipped onto the loop 7a and is movable with the followers 17 in the directions indicated by the arrow Pf2. The distal end portion of each of the two guides 13 can guide the distal end portion of a discrete conductor assembly 4 so that the terminals of the assemblies 4 can map the adjacent portions of the internal surface of a body organ. The provision of a distancing element between the followers 17 of FIG. 13 further enhances the stability of the three-dimensional framework established by the loop 7a and by the distal end portions of the two guides 13.

The catheter 1 of FIGS. 12 and 13 can be modified in a number of ways. For example, the three guides 7, 13, 13 which are shown in FIG. 13 can be used jointly with a further guide corresponding to the guide 7' of FIG. 8. The loop (7a') of such further guide can serve merely as a means for further stabilizing the framework established by the loop 7a and the distal end portions of the guides 13 and/or as a means for establishing an additional path for the movement of the distal end portion of a conductor assembly (e.g., an assembly relative to the adjacent internal surface of a heart or another body organ.

It is also possible to modify the catheter 1 of FIGS. 12 and 13 in such a way that the modified catheter includes the guides 7 and 7' of FIG. 8 and the two guides 13 of FIG. 13. The distal end portion of one of the guides 13 can be provided with a follower which is slidable along the loop 7a of the guide 7, and the distal end portion of the other guide 13 can be provided with a follower which is slidable along the loop 7a' of the guide 7'.

The strands of the three guides 7, 13, 13 shown in FIG. 13 can be confined in a single lumen of the sheath 2 or each such strand can be confined in a discrete lumen. Alternatively, a first lumen can be provided to confine two of the three strands and a second lumen can be provided to confine the third strand.

Figure 14:
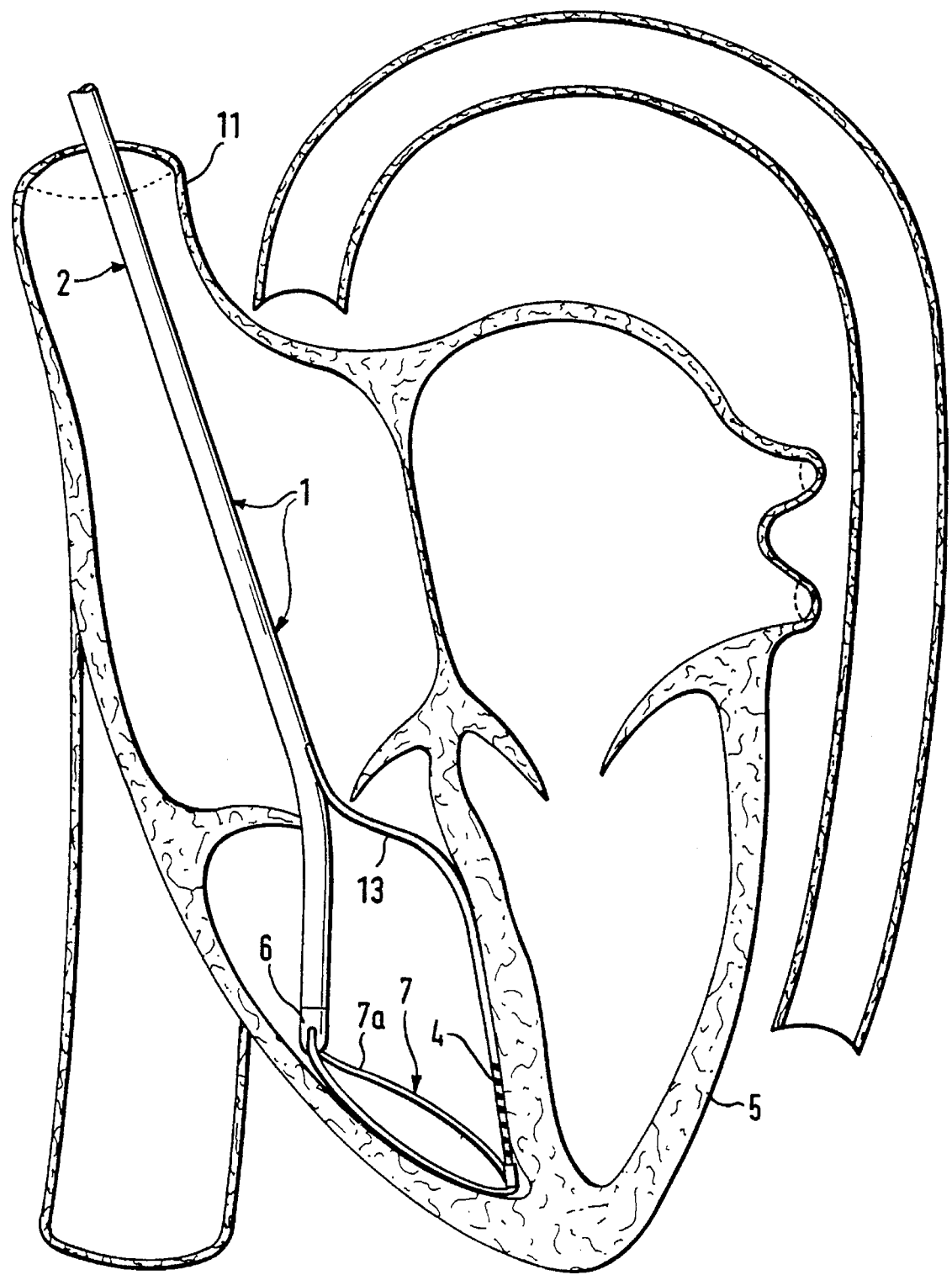
FIG. 14 is a view similar to that of FIG. 8 but with one of the guides omitted, all as described and shown in the parent application.

FIG. 14 shows the catheter of FIG. 8 but with the guide 7' and its loop 7a' omitted or withdrawn. The loop 7a of FIG. 14 occupies the same position as the loop 7a' of FIG. 8.

An advantage of the catheters of the type shown in FIGS. 1 to 14 is their versatility. Thus, the size of the single loop (7a or 7a') or the sizes of plural loops can be selected upon completed introduction of the distal end 6 of the sheath 2 into a heart or into another body organ. This ensures that the loop or loops closely follow the outline(s) of the adjacent portion(s) of the internal surface of the organ and establishes or establish one or more optimal paths for the advancement of one or more conductor assemblies which are utilized to carry out a mapping or scanning, ablating, stimulating and/or other operation. By selecting the size(s) of the loop(s) upon introduction of the distal end 6 of the sheath 2 into a body organ, the person in charge can ensure simple, convenient and rapid introduction of the distal end 6 to an optimum position for reliable anchoring of the loop or loops in a chamber by the expedient of thereafter increasing the size(s) of the loop(s) so that each loop remains in the selected position during advancement of the distal end portion of a conductor or conductor assembly therealong. By way of example, the distal end 6 can be introduced into the right auricle of a heart to ensure that the single loop or one of plural loops will adequately contact and will be reliably maintained in contact with the right ventricular valve during the following mapping, ablating, signal receiving or impulse transmitting operation.

If a catheter of the type shown in FIGS. 1 through 14 is to be used to carry out a mapping operation along one side of a cardiac valve (reference may be had, for example, to FIG. 1), the entire ring of such valve can be mapped by a conductor assembly 4 or 4' having, for example, six, eight or ten terminals or poles 20 at the respective distal end portion 4a or 4a'. The person in charge knows the number of terminals 20 and their mutual spacing along the distal end portion 4a or 4a', and such terminals are caused to advance along an arc of at least close to 360° in a direction from the first end of the loop (e.g., the first end 8 of the loop 7a) toward the outlet 15a of the lumen 15 or in the opposite direction. The terminals 20 transmit electric signals to a recording apparatus, not shown. Since the material (e.g., wire) of the guide 7 or 7' is readily flexible, the loop or loops do not interfere with pulsating movements of the heart but their material is sufficiently rigid to establish a predictable path for the advancement of the distal end portion 4a or 4a' of a conductor assembly 4 or 4' therealong. As already mentioned above, the wire which is used for the making of the guide 7, 7" or 13 can be made of a metallic or other suitable material (such AS NITINOL, TINEL or a monofilamentary plastic material). A1 that is necessary is to ensure that the wire exhibits the aforementioned desirable characteristics regarding its flexibility, resiliency, memory and dimensions.

The catheters which are shown in FIGS. 6 to 14 exhibit the advantage that the provision of one or more additional guides (such as 13 and/or 13") even more reliably ensures that the selected path or paths for the distal end portion(s) of one or more conductor assemblies will remain unchanged in the course of a mapping or other operation. The loop 7a or 7a' or the loops 7a and 7a' then serve to properly position the distal end portion(s) of the guide(s) 13 and/or 13" or vice versa, depending upon whether the distal end portion of a conductor assembly is caused to advance along the loop 7a or 7a' or along the distal end portion(s) of the guide(s) 13 or within the distal end portion of the guide 13". For example, and referring again to FIG. 6, the size of the loop 7a can be selected in such a way that the loop maintains the distal end portion 13a of the guide 13 in an optimum position for the advancement of the distal end portion 4a' of the conductor assembly 4' along a selected portion of the surface bounding the respective chamber of the heart 5. At the same time, the guide 13 maintains the loop 7a in an optimum position to guide the distal end portion of a conductor assembly (such as the distal end portion 4a of the assembly 4) along at least one-half of the adjacent side of the valve at the distal end 6 of the sheath 2. Thus, the catheters which are shown in FIGS. 6 to 14 render it possible to dispense with regulatable electrodes and to complete a mapping or other operation within a fraction of the time which is required to complete the same operation with regulatable electrodes.

The feature that the size of the loop 7a or 7a' can be varied infinitely and that the length of the exposed distal end portion of a guide 13 or 13" is also variable at will further ensures that such size or sizes and/or length or lengths can be rapidly selected for the purpose of establishing one or more optimal paths for the advancement of the distal end portion or portions of one or more conductor assemblies. The three-dimensional frameworks composed of the guides shown in FIGS. 6 to 14 are particularly suitable to ensure the establishment of one or more optimal paths for the advancement of one or more conductor assemblies (i.e., one or more groups of terminals or poles) in the course of a mapping or other operation. This is due to the fact that the loop or loops of one or more guides 7, 7' reliably hold one or more guides 13 or 13" in selected positions and vice versa.

The diameters of the wires which are used to make the guides 7, 7' and 13 are preferably identical, and this preferably also applies for the diameters of lumina defined by the conductor assemblies 4 and 4'. This ensures that the assembly 4 or 4' can be caused to slide along the guide 7, 7' or 13.

The terminals or poles 20 can serve for point-by-point mapping of one or more selected portions of a body organ, i.e., to transmit appropriate signals in the course of mapping an internal surface of a heart, and/or for the determination of electrical potentials at various points of a heart.

Though it is also possible to select the length of a guide 7 or 7' in such a way that the loop 7a or 7a' constitutes a median portion of the guide and the guide further comprises two elongated strands (such as 9) each of which is slidable in the single lumen (15) or in one of several lumina in the sheath 2, the constructions which are shown in FIGS. 1 through 14 are preferred at this time because only one strand of each of the guides 7 and 7' must extend from the distal end 6 and all the way to the proximal end 2a of the sheath 2.

The provision of a preformed section 14 as part of the guide 7 or 7' constitutes an optional but desirable and advantageous feature of the respective catheter. The section 14 ensures that the loop 7a or 7a' automatically assumes or tends to assume a desired position (in a plane which is inclined relative to the distal end 6 of the sheath 2) so that the loop 7a or 7a' can be rapidly and predictably located in an optimum position for the advancement of the distal end portion of a conductor assembly along a predetermined path. In the absence of the preformed section 14, the positioning of the loop 7a along the upper side of left-hand heart valve shown in FIG. 6 would require extensive manipulation in order to flex the loop 7a from a plane which includes the axis of the distal end 6 of the sheath 2 into a plane which is shown in FIG. 6, namely at an oblique angle to the distal end 6. At the same time, the provision of the section 14 does not complicate the introduction of the distal end 6 of the sheath 2 into or its extraction from a chamber in a body organ or from a passage defined by a blood vessel or another conduit because the wire of the guide 7 is sufficiently flexible to permit retraction of the entire loop 7a (or of a major portion of such loop) into the lumen 15. However, when the loop 7a is even partially expelled from the lumen 15, the section 14 immediately tends to move the loop into a plane which is inclined relative to the distal end 6 of the sheath 2.

Though it is possible to affix one end of the loop (such as the end 8 of the loop 7a shown in FIG. 4) to the external surface of the distal end 6 of the sheath 2, the provision of the socket 16 is preferred at this time because the end 8 of the loop 7a (i.e., of the wire of which the guide 7 is made) is less likely to interfere with the introduction of the distal end 6 into or with the extraction of such distal end from a chamber in the heart 5 or another organ. Furthermore, the end 8 of the loop 7a is less likely to become detached from the distal end 6 if it is anchored in the material of the sheath 2.

Each follower 17 could be fixedly secured to a selected portion of the loop 7a or 7a'. However, the provision of a follower which is slidable along the loop exhibits the advantage that the entire loop can be retracted into the lumen 15 of the sheath 2. Referring again to FIG. 6, if the follower 7 is slidable along the loop 7a, such loop can be practically completely retracted into the lumen 15 and the follower 17 is then located at the outlet 15a. Thus, only a very short or a relatively short portion of the guide 13 remains exposed (namely that part of the distal end 13a which extends along a straight line between the outlets 2b and 15a of the sheath 2). Another advantage of a follower 17 which is slidable along the loop 7a or 7a' is that the distal end portion 13a of the guide 13 can be moved to an infinite number of positions in each of which the distal end portion 13a extends from the outlet 2b to a selected part of the loop 7a. In this way, a conductor assembly (such as the assembly 4' shown in FIG. 6) can map a circumferentially complete portion of the surface bounding the respective chamber in the heart 5 while the position of the loop 7a remains unchanged. All that is necessary is to shift the follower 17 along the loop 7a.

If the catheter is used as a means for transmitting to the heart 5 a series of stimulating impulses, such impulses can be transmitted by the conductor assembly 4 or 4' or by a tubular conductor comprising a single terminal or a number of conductors less than the number normally used to make a tube forming part of the conductor assembly 4 or 4'.

Regardless of whether a conductor assembly 4 or 4', or a flexible sleeve-like moving device, is used to shift the follower 17 along the loop 7a or 7a', such conductor assembly or such flexible sleeve also contributes to the stability of the three-dimensional framework which includes the guide 7 and/or 7' and one or more guides 13. Thus, the loop 7a or 7a' is even less likely to be displaced relative to the adjacent portion of the internal surface of a body organ if at least a part of such loop is surrounded by the means for shifting the follower to any one of a practically infinite number of different positions. If the follower is to be shifted by moving means other than the conductor assembly 4 or 4', such moving means can constitute an elongated flexible hose which can be slipped onto the guide 7 or 7' to move the follower along the loop 7a or 7a'. If the follower is to be shifted by the distal end portion of a conductor assembly (such as the assembly 4 or 4'), the conductor assembly can perform a plurality of different functions, namely moving the follower along the loop 7a or 7a', stiffening the three-dimensional framework including the guide 7 and/or 7' and one or more guides 13, and carrying out a mapping operation along the loop 7a or 7a'. The mapping operation along the distal end portion 13a of the guide 13 shown in FIG. 6 can precede or follow the mapping operation along the loop 7a or such mapping operations can be carried out simultaneously.

Ablation of unhealthy cells can immediately follow a mapping operation. Thus, the mapping operation can serve to determine the presence and the location or locations of afflicted cells, and the following ablating operation is carried out to destroy the thus detected defective cells. All that is necessary is to connect at least one conductor 3 with the energy source 103 so that the corresponding terminal or pole 20 can be utilized to carry out the ablating operation. Though it is also possible to employ a discrete conductor or a discrete conductor assembly solely for the purposes of ablation, the utilization of one or more conductor assemblies (such as 4 and 4') having conductors connectable to the energy source 103 even further enhances the versatility of the catheter because the conductor assembly 4 and/or 4' can also serve to carry out a mapping operation. The energy source 103 can constitute a conventional high-frequency generator, and the signals from the temperature sensor 19 are transmitted to the circuit 103a which regulates the operation of the generator 103 in a manner not forming part of the invention. The circuit 103a prevents the temperature at the pole or terminal 18 from exceeding a predetermined maximum value. The predetermined temperature is selected in such a way that it suffices to carry out the ablating operation but is lower than that which could prove damaging to the neighboring (healthy) tissue.

Certain sections (corresponding to the section 14 shown in FIG. 2) of the plural loops 7a and 7a' can be selected in such a way that the loops 7a and 7a' exhibit the tendency to extend from the sockets in the distal end 6 to opposite sides of the sheath 2. It has been found that an orientation of the loops 7a and 7a' shown in FIG. 8 exhibits a number of advantages. Thus, these loops enable the distal end portion of a conductor assembly (such as 4 or 4') to carry out a number of mapping operations all the way around the respective portion of the internal chamber of the heart 5. Furthermore, the distal end portion of a conductor assembly which is caused to slide along the loop 7a or 7a' can be used to transmit to the heart 5 a series of stimulating impulses while the distal end portion of the conductor assembly which is caused to slide along the loop 7a' or 7a can be used to carry out a mapping or ablating operation. It is also possible to provide the distal end 6 of the sheath 2 with a total of three outlets, namely an outlet 2b for the guide 13, an outlet 15a for the guide 7 and an outlet (e.g., adjacent the outlet 15a) for the guide 7'. The provision of two or more guides (such as 7 and 7') which are installed in such a way that they can be caused to develop loops at the distal end 6 of the sheath 2 exhibits the advantage that it is even less likely to permit undesirable shifting of the path or paths for the distal end portion(s) of one or more conductor assemblies when the catheter is used to carry out a mapping, ablating or other operation in a heart, i.e., in an organ which performs pulsating movements during treatment or during mapping.

An advantage of a catheter which embodies the structure of FIGS. 12 and 13 is that it is even more likely to ensure that the paths for the advancement of the distal ends of electrode assemblies along the one and/or the other guide 13 and/or along the loop 7a remain unchanged in the course of a mapping or other operation while the organ (heart 5) performs a series of pulsating movements. The sheath, the plural guides 13 and the loop 7a together constitute a substantially basket-shaped framework which can yield so that it does not interfere with the pulsating movements of the heart but is sufficiently stable to continue to maintain the loop 7a and the distal end portions of the guides 13 in selected positions.

A catheter which embodies the structure of FIGS. 12 and 13 exhibits the additional advantage that it establishes a plurality of different paths for the advancement of the distal end portion(s) of one or more conductor assemblies along the internal surface of a body organ. The number of paths can be further increased by combining the features of the catheters of FIG. 8 and FIGS. 12–13, i.e., by employing a plurality of loops. Such plural loops can cooperate with the distal end portions of two or more guides 13 in order to further stabilize the three-dimensional framework and/or to establish one or more additional paths for the advancement of the distal ends of conductor assemblies.

The catheter of FIG. 9 is also susceptible of numerous additional modifications. For example, the tubular guide 13" can be utilized together with one or more (non-tubular) guides 13 to further stabilize the three-dimensional framework including the loop 7a and the guide 13" as well as to establish one or more additional paths for the distal end portions of conductor assemblies. As already mentioned above, the catheter of FIG. 9 exhibits the advantage that the substantially J-shaped or hook-shaped distal end portion 22 of the conductor means 21 can be caused to map that side of the heart valve which faces away from the loop 7a, i.e., a side which cannot be mapped or treated with conventional catheters or which can be mapped or treated with conventional catheters only by entrusting the task to highly skilled practitioners and within an inordinately long interval of time.

It is further possible to combine the features of the several illustrated and described catheters in a manner not specifically pointed hereinabove. All in all, in spite of their simplicity, the catheters shown in FIGS. 1 through 14 and described in the preceding passages of the specification are more versatile than heretofore known catheters, they can be used to map and/or otherwise treat those parts of body organs which cannot be readily mapped and/or otherwise treated with previously known catheters, and the mapping and/or other operation(s) can be completed within surprisingly short intervals of time. Each of the aforedescribed catheters can be readily introduced into a heart or into another body organ through a blood vessel or through another body passage, and the introduction and/or extraction of the catheter is atraumatic because at least the major part of each guide can be completely or nearly completely retracted into the sheath 2. The properly inserted and enlarged loop 7a and/or 7a' can establish a reliable temporary force-locking or form-locking connection between the catheter and the body organ. Such connection between the catheter and a human or other animal heart does not affect the ability of the heart to carry out its pulsatory movements.

Another advantage of the catheter is that it can be mass-produced at a reasonable cost. Thus, in its simplest form, the catheter will comprise the sheath 2, the guide 7 or 7', and the conductor assembly 4 or 4'. Moreover, the versatility of the catheter can be enhanced in a simple and inexpensive way, e.g., by employing two guides (such as 7 and 7') each of which can form a loop (7a or 7a'), by adding one or more guides 13 and/or by adding one or more guides 13".

Another material which can be used to make the guide 7 and/or 7' and/or 13 is steel. The diameter of the metallic or plastic wire of which the guide 7 and/or 7' and/or 13 is made can be in the range of between 0.3 and 0.5 mm.

If a pronounced versatility of the catheter is not important, the distal end portion of a conductor assembly (such as the end portion 4a of the conductor assembly 4) can be affixed to the distal end 6 of the sheath 2, i.e., the conductor assembly need not be mounted for movement relative to the loop of the guide. The utilization of a catheter wherein the distal end portion of a conductor assembly is movable relative to the loop is preferred because the cross-sectional area of the distal end 6 of the sheath 2 can be reduced accordingly. Furthermore, the conductor assembly need not be as flexible as the guide 7, 7' or 13.

The sheath 2 can be provided with a row of two or more longitudinally spaced apart outlets for two or more guides 7 or 7' which are spaced apart from each other in the longitudinal direction of the sheath. Referring, for example, to the catheter of FIG. 8, the first and second ends of the loops 7a and 7a' can be spaced apart from each other in the longitudinal direction of the sheath, i.e., one of the two loops can be spaced apart from the loop 7a or 7a' of FIG. 8 in a direction toward the proximal end of the sheath. This renders it possible to map and/or ablate at two or more circumferentially complete portions of the surface bounding the chamber which receives the distal end 6 of the sheath 2 of FIG. 8. The spacing of two or more loops in the longitudinal direction of the sheath 2 can be such that the loop or loops 7a, 7a' assumes or assume the position(s) shown in FIG. 8 while a further loop engages the underside of the heart valve above the distal end 6 of the sheath 2 shown in FIG. 8. One or more loops can be provided between the further loop and the loops 7a, 7a' of FIG. 8.

It is also possible to replace at least one of the conductor assemblies 4, 4' and 21 with an assembly composed of or comprising electrode pins and/or electrode rings. At least one of the guides can further serve as a means for facilitating the introduction of one or more inflatable balloons which serve as additional means for reliably maintaining the respective guide or guides in optimum positions for advancement of conductor assemblies along predetermined paths or for other purposes. This will be described in detail with reference to FIGS. 15 through 22. For example, one or more balloons can be slipped onto or provided on the distal end portion 13a of the guide 13 shown in FIG. 6 to come into large-area contact with the adjacent portion of the internal surface of the heart 5. If the catheter employs or can be combined with one or more balloons, such catheter can constitute or include an endoscope including at least one bundle of optical fibers, all as will be described in full detail with reference to FIGS. 15 through 22. For example, a catheter including or constituting an endoscope can be utilized to permit inspection for the purposes of ascertaining the presence or absence of the calcification of heart valves, to inspect the condition of lesions which develop as a result of ablation and/or for other purposes.

The catheter of FIG. 9 can be modified by selecting the dimensions of the lumen of the tubular guide 13" in such a way that it can confine two conductors or conductor assemblies 21 each having a substantially J-shaped distal end portion 22. This renders it possible to complete the mapping or the ablation at the underside of the left-hand valve in the heart 5 of FIG. 9 within an even shorter interval of time. Furthermore, two or more substantially J-shaped distal end portions 22 are even more likely to maintain the loop 7a of FIG. 9 in a desired position during mapping or during ablation at the upper side of the valve which is located beneath the loop 7a of FIG. 9.

At least one of the described and illustrated conductor assemblies can be furnished with the aforediscussed temperature sensor 19, with one or more pressure sensors and/or with one or more pH sensors. As a rule, the exact nature of the conductor assembly or conductor assemblies will depend upon the electro-physiological tasks which are to be carried out by the selected catheter.

To summarize: The improved catheter can be utilized for mapping and/or for ablation in the chamber or chambers of a heart or another body organ and includes a flexible sheath the distal end of which can be advanced through a blood vessel or another body passage into a selected chamber of a heart or into an internal space of another body organ. A wire-like guide of the catheter has a distal end portion affixed to the distal end of the sheath and is slidable in a lumen of the sheath so as to form a loop adjacent to and located externally of the distal end of the sheath. The guide and its loop are used as a means for steering or directing the distal end portion of a tubular electrical conductor assembly to any one of a number of different positions relative to the surface surrounding a heart chamber or another internal space of a body organ. The size of the loop is reduced prior to introduction of the distal end of the sheath into and prior to extraction of the distal end of the sheath from a selected chamber or another internal space. The catheter can be further provided with a second guide which serves to form a second loop at the distal end of the sheath and/or with one or more further guides having distal end portions slidable along the single loop or along one of plural loops. The catheter can employ one, two or more electrical conductor assemblies.

FIGS. 15 through 22 illustrate several embodiments of an endoscope 1A which can employ several constituents of mapping and ablation catheters 1 shown in FIGS. 1 to 14. All such parts of the endoscope of FIGS. 15 to 22 which are identical with or clearly analogous to the corresponding parts of mapping and ablation catheters of FIGS. 1 to 14 are denoted by similar reference characters. Furthermore, all such parts of several embodiments of the improved endoscope 1A of FIGS. 15 to 22 which are identical with or clearly analogous to each other are also denoted by similar reference characters.

Figure 15:
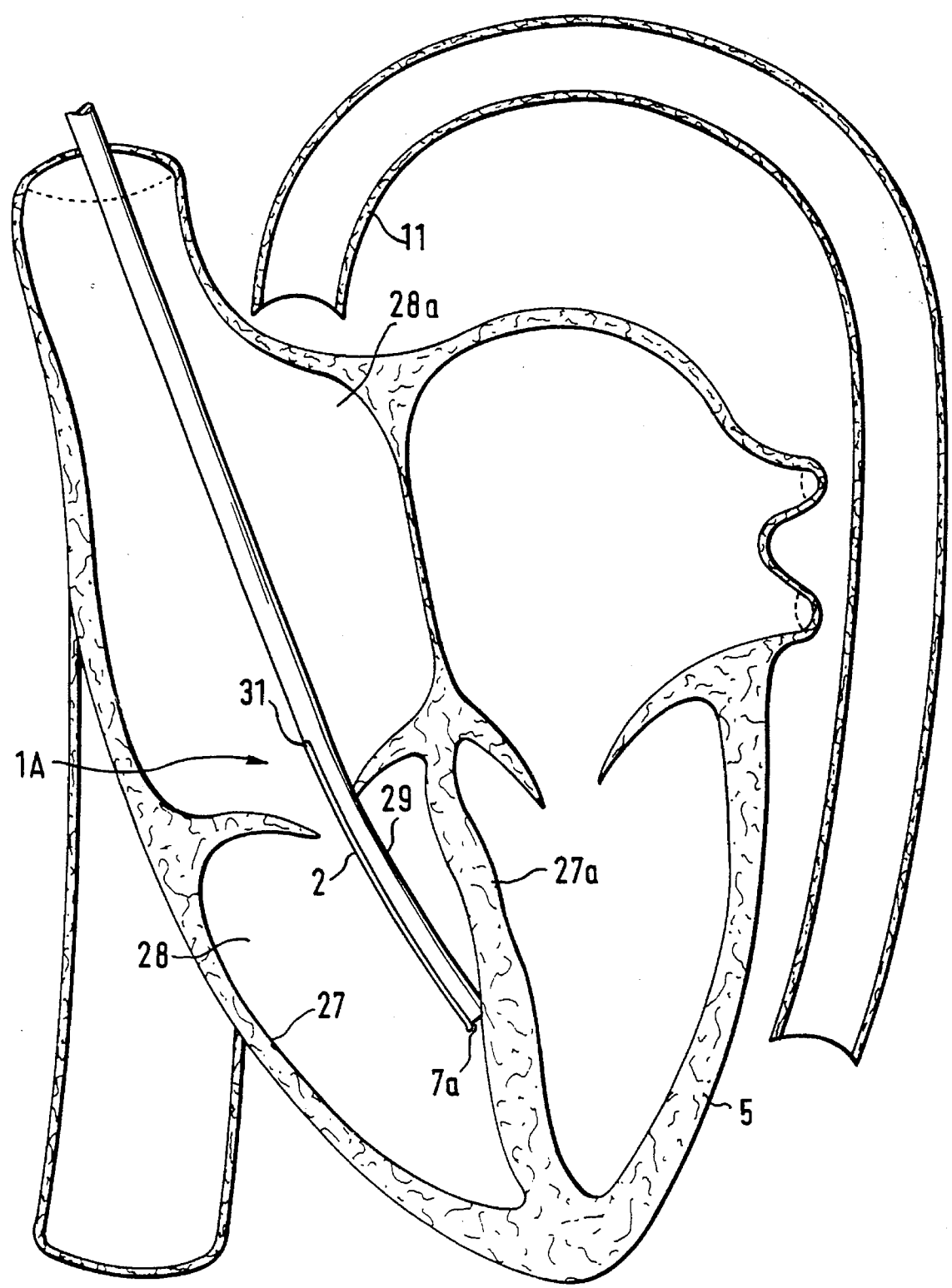
FIG. 15 is a schematic sectional view of a heart and further shows a portion of an endoscope which embodies one form of the invention and the distal end of which is inserted into a chamber of the heart, the balloon being collapsed and the sheath for the balloon as well as a loop of a flexible guide forming part of a mechanical device or frame for holding the expanded balloon in a selected position being retracted into the distal end of the tube.
Figure 16:
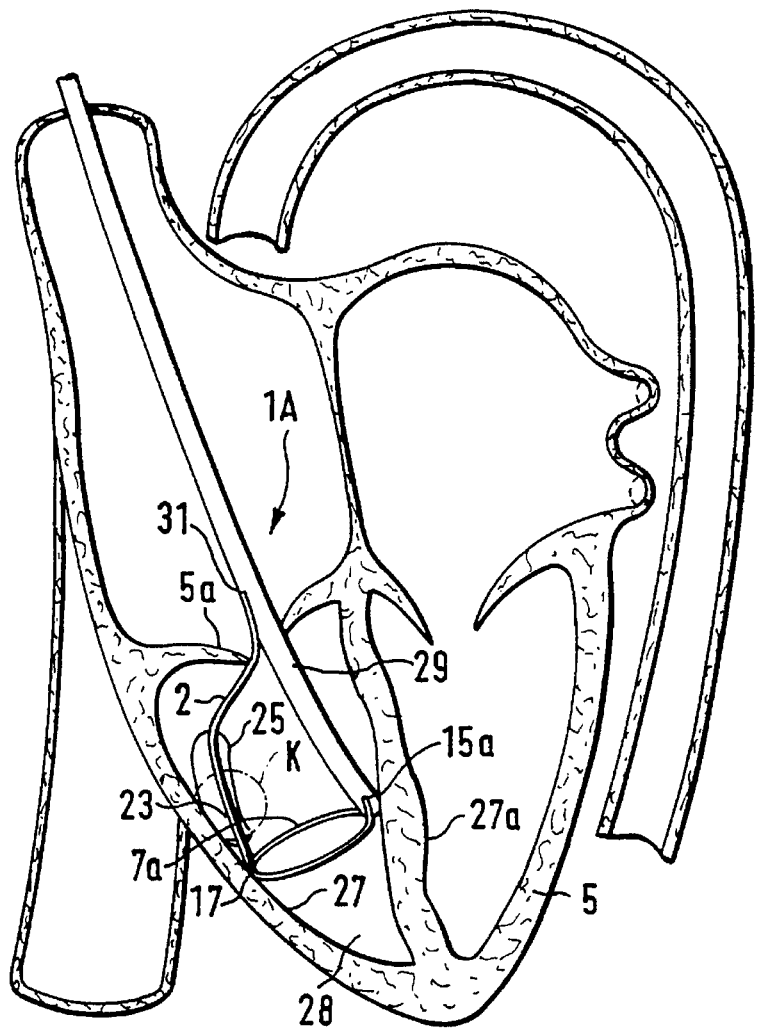
FIG. 16 is a smaller-scale view of the structure which is shown in FIG. 15 but with the loop and the distal end of the sheath shown in extended positions and with the balloon inflated adjacent a selected portion of the surface bounding the chamber of the heart.
Figure 17:
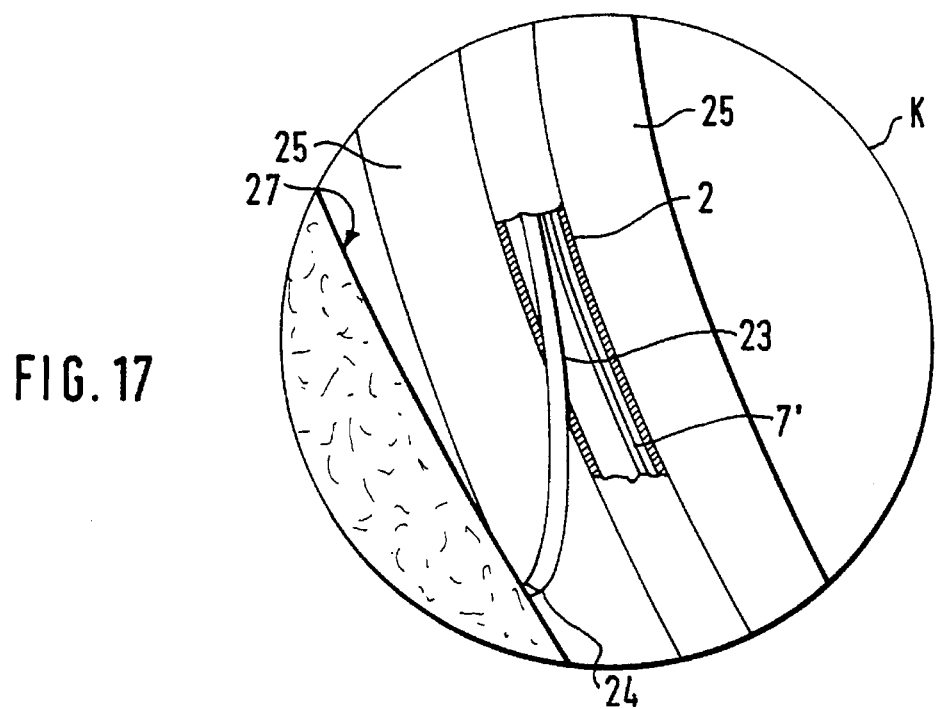
FIG. 17 is an enlarged view of a detail within the circle K in FIG. 16.
Figure 22:
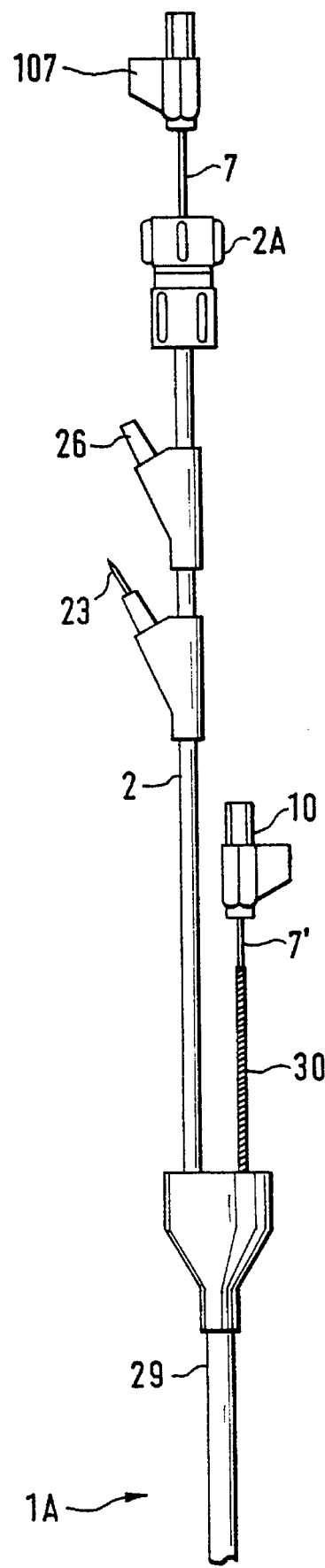
FIG. 22 is an enlarged view of the proximal end of an endoscope which embodies the present invention, there being shown the proximal ends of two wire-like guides, certain optical elements of the endoscope and the inlet of the device which defines a path for the flow of a fluid into and from the balloon at the distal end of the sheath.

The endoscope 1A which is shown in FIGS. 15 to 17 comprises an elongated flexible tube 29 having a distal end which is introduced into an internal space of a body organ here shown as a chamber 28 in a human or other animal heart 5. The tube has one or more lumina one of which confines an intermediate portion of a longitudinally movable sheath 2 having a lumen (shown in FIG. 17) for a plurality of elongated flexible light- and image-transmitting conductors 23 having distal ends 24 confined in an expandable and collapsible balloon 25. Each conductor 23 can constitute an optical fiber or light guide made of glass or other suitable material. The endoscope 1A can be utilized with equal or similar advantage for illumination and imaging of surfaces in other internal spaces e.g.; within a blood vessel (such as an aorta) or another passage or chamber in a body organ. As is well known in the art of endoscopes, some of the conductors 23 serve to transmit light to the surface to be illuminated and the remaining conductors transmit images of the illuminated portion or portions of such surface The inflatable and deflatable or collapsible balloon 25 confines the distal ends 24 of the conductors 23 so that such distal ends cannot come into actual contact with the adjacent surface of a wall 27 forming part of the heart 5 and surrounding a portion of the cavity 28. FIG. 22 shows the inlet 26 of a conduit forming part of the means for establishing a path for the flow of a fluid (such as a liquid) which is introduced into the inlet in order to inflate the balloon 25 and which permits the fluid to escape from the aforementioned path when the balloon 25 is being deflated. The inlet 26 is located at the proximal end of the flexible tube 29 and the conduit 26 extends through the sheath 2 all the way to the balloon 25. The means for inflating and deflating the balloon can include a lumen which is provided in the sheath 2 and has an inlet 26 at the proximal end of the tube 29. The manner in which the fluid which is to be admitted into a deflated balloon 25 is pressurized for introduction into the inlet 26 is known and is not shown in the drawings.

It is clear that the material of the balloon 25 transmits radiation so that it does not interfere with the illumination and imaging of those portions of an internal surface (such as that bounding the heart chamber 28 shown in FIGS. 15 and 16) when the endoscope 1A is in actual use. FIGS. 16 and 17 further show that, when the balloon 25 is inflated, a portion of its external surface abuts a portion of the internal surface of the adjacent wall 27 so that the balloon prevents blood from contacting the distal ends 24 of the conductors 23 but (even when inflated) offers little resistance to the flow of blood into and/or from the chamber 28. The distal ends 24 of the conductors 23 are adjacent the inner side of that portion of the inflated balloon 25 which abuts the adjacent portion of the wall 27. However, the diameter of the inflated balloon is but a fraction of the width of the respective portion of the chamber 28.

Accurate positioning of the balloon 25 in a chamber 28 is facilitated by the provision of an elongated wire-like guide 7 which enters the proximal end of the sheath 2 and carries a loop 7a (or can be caused to develop a loop 7a, e.g., in a manner as described in connection with the catheter 1 of FIGS. 1 to 14) serving to maintain the distal ends 24 of the conductors 23 in selected positions. Such accurate positioning is desirable and advantageous not only in order to ensure that the conductors 23 will illuminate and image selected portions of surfaces bounding selected spaces in body organs but also because the inflated balloon 25 cannot interfere with the flow of body fluids, e.g., of blood in blood vessels and/or in a chamber of the heart 5. The balloon is reliably prevented from interferring with or from stopping the flow of body fluid by the expedient that its space requirements in the inflated condition are but a small fraction of the capacity of an internal space which is to receive the distal ends 24 of the conductors 23.

The tube 29 can at least partially confine the sheath 2 and the loop 7a of the guide 7 during introduction of the distal end of the endoscope IA into as well as during extraction of such distal end from a body cavity. As can be seen, for example, in FIG. 16, the distal end of the tube 29 can cooperate with the distal end of the sheath 2 and with the loop 7a of the guide 7 to establish a substantially cage-like support or frame for the inflated balloon 25. As also shown in FIG. 16, the dimensions of the cage like support or frame are or can be such that the component parts of the support contact widely spaced apart portions of the surface bounding the chamber 28. Thus, the distal end of the properly inserted tube 29 engages a small portion of the right-hand wall 27a bounding the chamber 28, whereas the central portion of the loop 7a engages the left-hand wall 27 bounding the same chamber 28. In addition, the loop 7a can engage a circumferentially complete portion of the surface bounding the chamber 28 because its material is readily deformable and is resilient so that the loop can closely follow the outline of the immediately adjacent portion of the surface bounding the chamber 28. Furthermore, and as already described with reference to FIGS. 1 to 14, the size of the loop 7a can be varied so that the loop can readily follow the outline of a surface bounding a relatively small or a slightly larger or much larger portion of an internal space. For example, the size of the loop 7a shown in FIG. 16 will be increased if the distal end of the tube 29 is moved upwardly so that it is located in a larger portion of the chamber 28. i.e., if the person carrying out the imaging operation desires to image a portion of the surface bounding the space or chamber 28 which is nearer to the left-hand heart valve shown in FIG. 16.

FIG. 15 shows the loop 7a of the guide 7 in a fully retracted or concealed position, i.e., in the single lumen or in the respective lumen of the tube 29. The extent to which the loop 7a is expelled from the distal end of the tube 29 or the size of the loop 7a which develops in response to shifting of the proximal end of the guide 7 relative to the proximal end of the tube 29 (e.g., by a handle 107 shown at the top of FIG. 22) will be selected in dependency upon the exact location of that portion of an internal surface which is to be imaged by the endoscope 1A.

Figure 20:
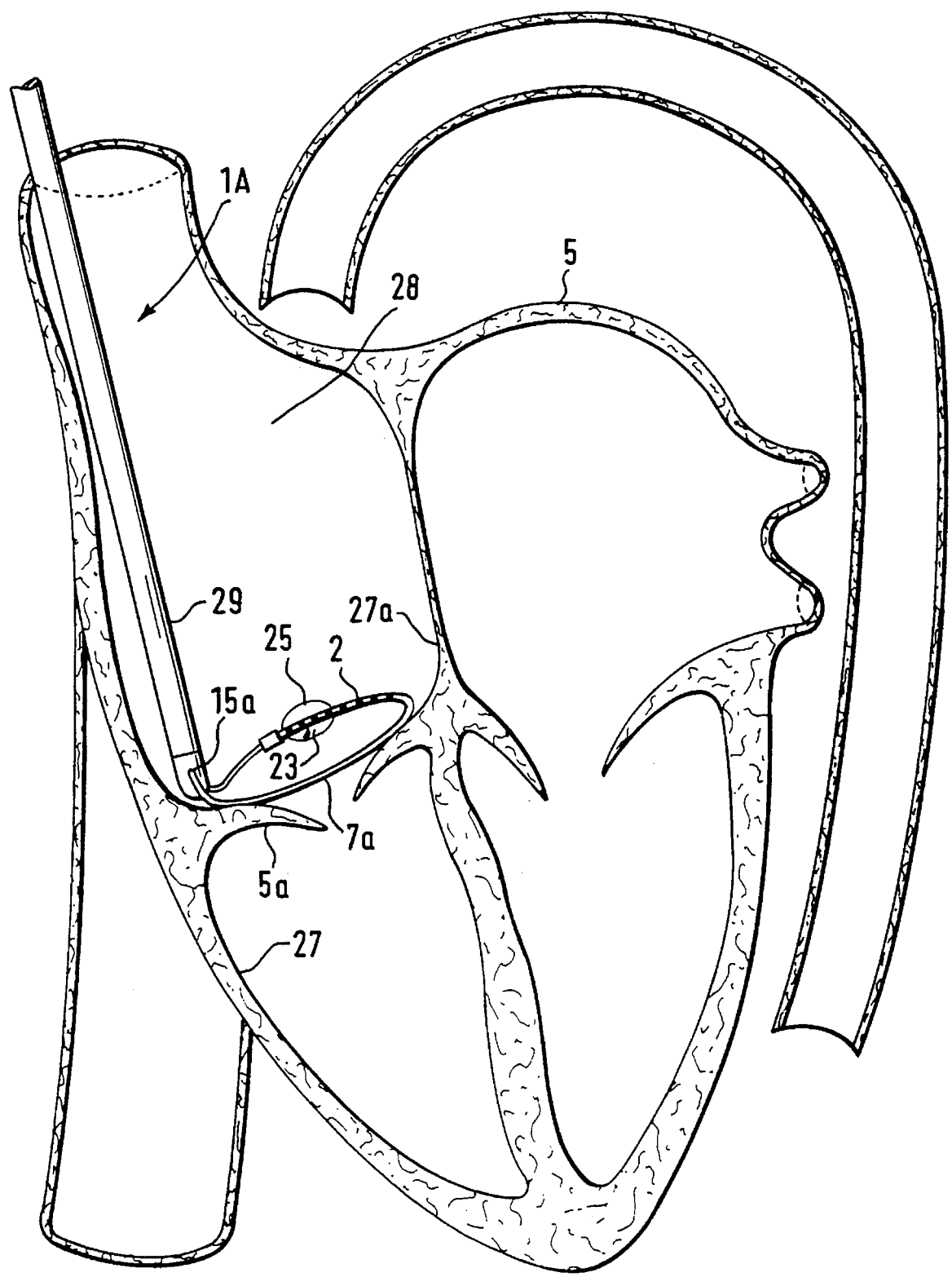
FIG. 20 is a view similar to that of FIG. 19 but showing a portion of a modified endoscope with the inflated balloon adjacent a portion of the loop at the distal end of the tube.

The loop 7a can be designed and mounted to perform one or more additional functions. For example, and as can be seen in FIG. 20, the sheath 2 can be provided with a lumen for the guide 7 and its loop 7a so that the balloon 25 can be shifted longitudinally of the loop 7a along an arc of close to 360°. At the same time, the loop 7a serves as an element of the frame or support for the balloon 25 as well as to ensure that the distal end of the properly inserted tube 29 remains in a selected position relative to the wall 27 of the heart 5. All that is necessary is to move the proximal end of the sheath 2 (such proximal end is shown in FIG. 22) relative to the proximal end of the tube 29 so that the balloon 25 is caused to move along the loop 7a of the guide 7. At such time, the position of the handle 107 for the proximal end of the guide 7 remains unchanged unless the person in charge desires to change the size of the loop 7a. An advantage of the endoscope 1A of FIG. 20 is that the balloon 25 can be moved up and down (with the distal end of the tube 29) as well as along an arcuate path (i.e., longitudinally of the loop 7a) while the axial position of the distal end of the tube 29 remains unchanged. Such movability of the balloon 25 up and down (as seen in FIG. 20) as well as circumferentially along the loop 7a enables the endoscope 1A to illuminate and image any desired portion of the surface bounding the chamber 28a in the heart 5 of FIG. 20.

Referring again to FIG. 16, it is possible to modify the endoscope 1A including the loop 7a which forms part of the guide 7 (or which is merely affirmed to the distal end of the guide 7) in a manner similar to that described in connection with the catheter 1 including the structure of FIGS. 12 and 13. Thus, and as can be seen in FIG. 17, a second wire-like guide 7' can extend through a lumen of the sheath 2 and its distal end can carry a follower (such as the follower 17 shown in FIG. 21) which is slidable along the loop 7a. In this manner, the balloon 25 can be moved along the distal end of the guide 7' toward and away from the follower, along the loop 7a by moving the follower longitudinally of the loop 7a, and jointly with the distal end of the tube 29. FIG. 16 shows that the distal end of the tube 29 is provided with an outlet 15a for the distal end of the guide 7 and its loop 7a, as well with an outlet 31 for the sheath 2 (i.e., for the distal end of the guide 7' and the balloon 25). As a rule, the ballon 25 will be expelled from the tube 29 through the outlet 31 prior to inflation and will be retracted into the tube 29 subsequent to deflation. A sleeve or the like (not specifically shown) can be used to move the follower at the distal end of the guide 7' longitudinally of the loop 7a. Such sleeve can perform the same function as the conductor assembly 4 of FIG. 11, i.e., to move the follower of the guide 7' along the loop 7a.

FIG. 17 further shows that the distal ends 24 of the conductors 23 extend laterally through an opening (e.g., a slot) in the adjacent portion of the sheath 2 so that they extend into a passage of the balloon 25. Moreover, the proximal ends of the conductors 23 can be connected with a handle (e.g., a handle corresponding to the handle 107 shown in FIG. 22) which renders it possible to move the distal ends 24 of the conductors 23 relative to the passage in the balloon 25.

Figure 18A:
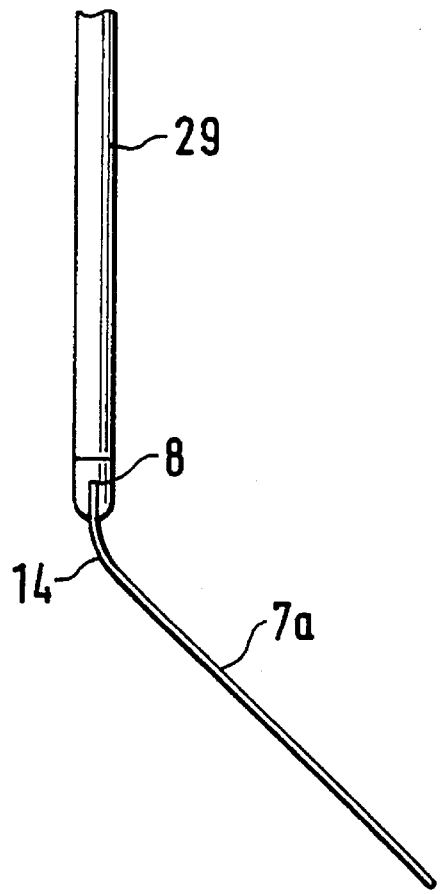
FIG. 18a is a side elevational view similar to that of FIG. 2 but showing a portion of the distal end of the tube in lieu of the sheath which is shown in FIG. 2.
Figure 18B:
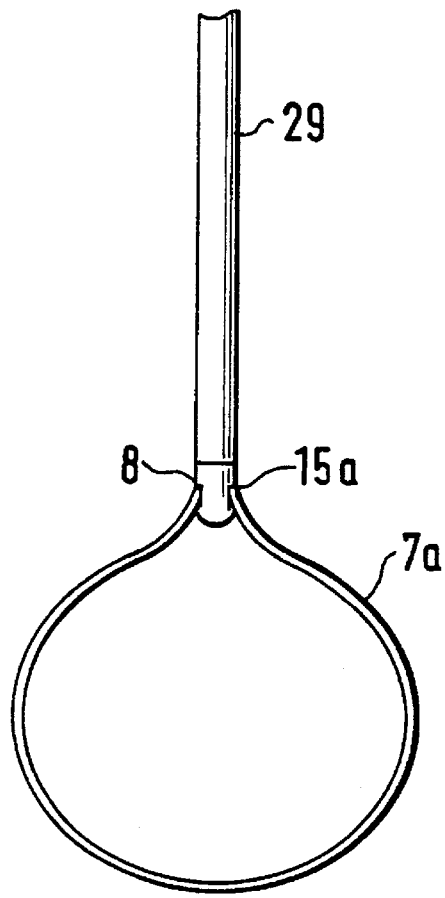
FIG. 18b is a view similar to that of FIG. 3 and shows the structure of FIG. 18a turned through an angle of approximately 90°.

FIGS. 18a and 18b show a structure which is similar to that shown in FIGS. 2 and 3 except that the guide 7 and its loop 7a are retractible into the tube 29 in lieu of the sheath 2. That portion of the guide 7 which is confined in the distal end of the tube 29 and is immediately adjacent the loop 7a makes an obtuse angle with the plane of the loop 7a when the latter is expelled from the tube 29 and is not subjected to any deforming stresses. This is due to the resiliency of the material of the guide 7 and its loop 7a and the provision of the aforementioned resiliently deformable section 14 adjacent that end of the loop 7a which is not anchored in the distal end of the tube 29.

Furthermore, and referring again to FIG. 16, if the section 14 of the guide (shown at 7 in FIG. 22) including the loop 7a is free to assume its intended position in or close to the plane shown in FIGS. 18a and 18b, the distal end of the tube 29 is automatically moved against the wall 27a and the central portion of the loop 7a automatically engages the wall 27 of the heart 5. The balloon 25 and the sheath 2 therefor are then movable along the second wire-like guide 7' (FIG. 17) along the wall 27 toward and away from the loop 7a, and the follower 17 at the distal end of the guide 7' is movable along the loop 7a, e.g., by a conduit performing the function of the conductor assembly 4 shown in FIG. 4, i.e., a device which can push or pull the follower 17 of the conduit 7' along the loop 7a. Since the exact distance of the loop 7a from the left-hand heart valve 5a of FIG. 16 can be selected by moving the distal end of the tube 29 toward or away from the valve 5a, the person in charge can illuminate and image the entire surface bounding the chamber 28.

The balloon 25 is inflated or reinflated as soon as the distal ends 24 of the conductors 23 reach the desired positions for illumination and imaging of a selected portion of the surface bounding the chamber 28. It is presently preferred to at least partially deflate the balloon 6 prior to each shifting of the balloon along the loop 7a, along the guide 7' and/or in response to longitudinal displacement of the distal end of the tube 29. Once the balloon 25 is inflated, the endoscope 1A is ready for use because the inflated balloon prevents blood from reaching the distal ends 24 of the conductors 23 and the balloon also keeps the body fluid away from that portion of the surface bounding an internal space which is being illuminated and imaged. At the same time, the balloon 25 and the support or frame therefor permit the body fluid to flow along its path, e.g., in a blood vessel or into and from a chamber in a human or other animal heart.

In the embodiment which is shown in FIG. 20, the sheath 2 which carries the balloon 25 directly surrounds the wire guide including the loop 7a. Thus, the outlet 15a in the distal end of the tube 29 renders it possible to retract the loop 7a as well as the sheath 2 and the balloon 25 into the single lumen or into one of several lumina in the tube 29 or to expel the loop 7a as well as the distal end of the sheath 2 and the balloon 25 from the distal end of the tube 29. The guide 7 which includes the loop 7a (or which develops the loop 7a upon expulsion of its distal end portion through the outlet 15a) is moved relative to the tube 29 in a first step until the loop 7a is fully exposed, and the sheath 2 is thereupon caused to slide along the exposed loop in a next-following step. The third step involves inflation of the balloon 25 when the distal ends 24 of the conductors 23 reach the selected or desired positions relative to the surface bounding the chamber 28a in the heart 5 of FIG. 20.

The sheath 2 can constitute a small-diameter conduit which conveys a liquid into or from the balloon 25. Alternatively, the sheath 2 can constitute a tube consisting of convoluted wire and surrounding a conduit which can convey a liquid into and from the balloon 25. For example, the sheath 2 can resemble the conductor assembly 4 which is shown in FIG. 4 and is slidable along the loop 7a of the guide 7.

Figure 19:
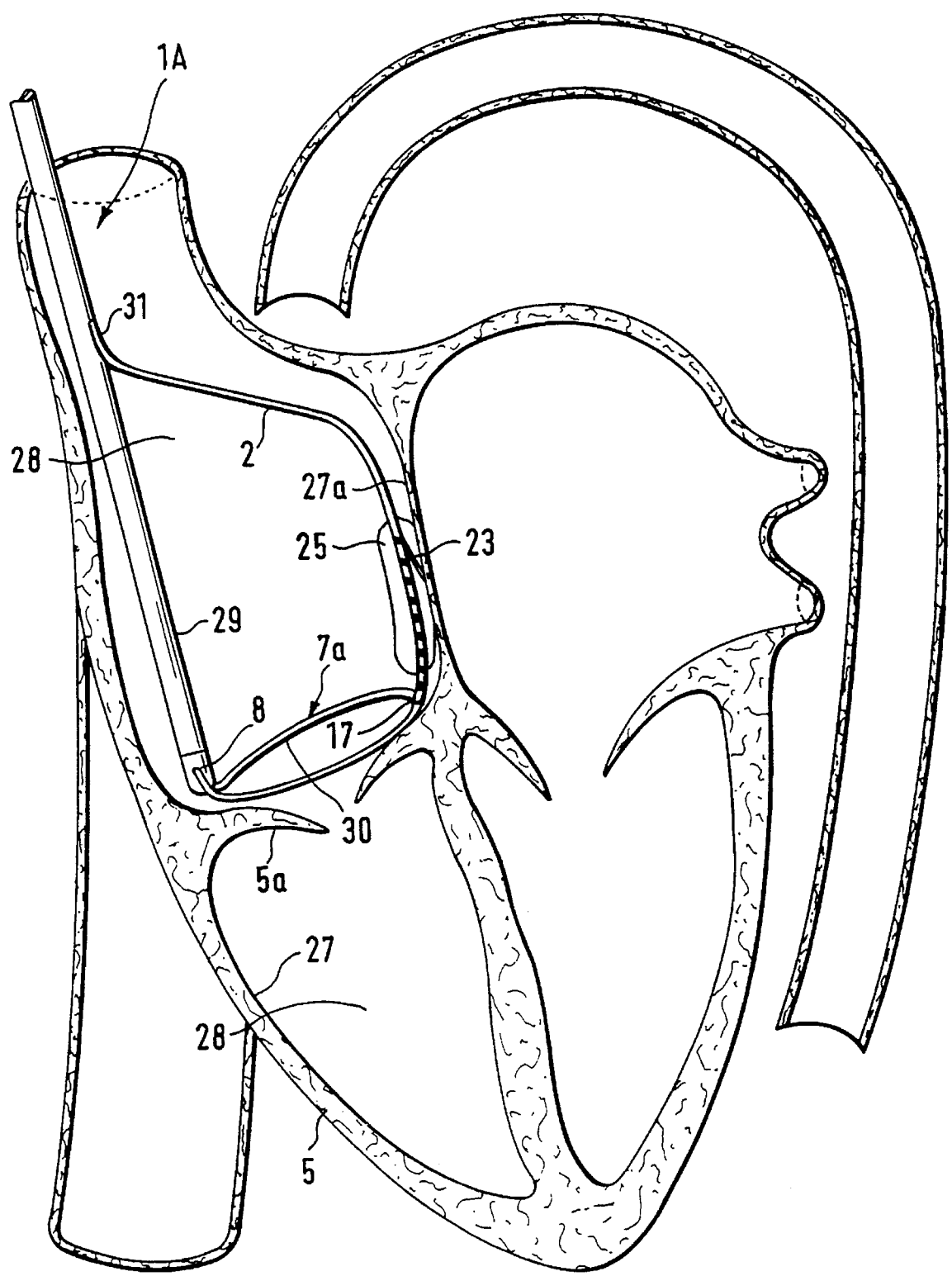
FIG. 19 is a view similar to that of FIG. 16 but showing the distal end of the improved endoscope in a different chamber of the heart so that the loop of the flexible guide is adjacent a heart valve.
Figure 21:
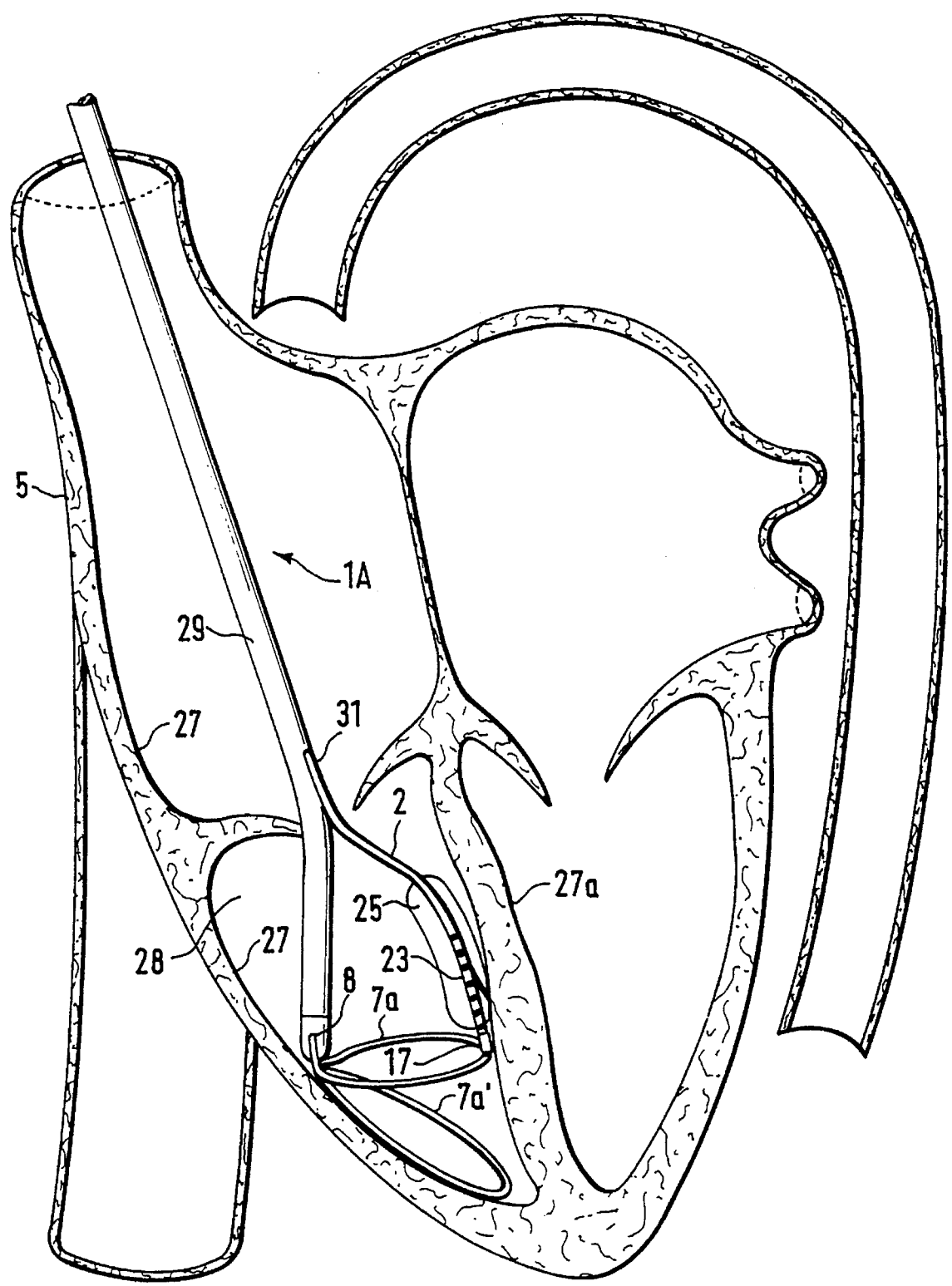
FIG. 21 is a view similar to that of FIG. 16, 19 or 20 but showing a portion of a further endoscope wherein the mechanical support for the distal end of the sheath includes two loops at the distal end of the tube.

The resiliently deformable section 14 of the guide 7 including the loop 7a of FIGS. 18a and 18b constitutes an optional but desirable feature of the improved endoscope 1A. Thus, the feature that the loop 7a automatically tends to move into a plane which makes an oblique angle with the elongated distal end of the tube 29 simplifies temporary achoring of the loop 7a in a selected portion of a body cavity. For example, the provision of the resiliently deformably section 14 simplifies the task of positioning the loop 7a in a manner as shown in FIGS. 16, 19, 20 and 21. Furthermore, such positioning of the loop 7a can be completed within a short interval of time. In FIG. 16, the loop 7a is located in the heart chamber 28 and is spaced apart from the valve 5a. In FIG. 19, the loop 7a is adjacent the upper side of the valve 5a, the same as in FIG. 20. In FIG. 21, the loop 7a is located in the heart chamber 28 and cooperates with the loop 7a' of the wire 7' to maintain the balloon 25 in a desired position adjacent the wall 27a.

As can be seen in FIG. 18b, the recess or socket for the end 8 of the loop 7a is located substantially diametrically opposite the outlet 15a through which the loop 7a can be retracted into the single lumen (or into the respective lumen) of the tube 29. Thus, the end 8 of the loop 7a is reliably anchored in the socket (corresponding to the socket 16 shown in FIG. 4) of the distal end of the tube 29 and the other end of the loop 7a can be moved relative to the outlet 15a, either to reduce the size of the loop 7a (e.g., at least close to zero) or to increase the size of the loop 7a when the need arises, e.g., when the loop 7a is to be moved from the position of FIG. 16 toward the valve 5a.

The material of the guide 7 and/or 7' and of the loop 7a or 7a' can be the same as described in connection with FIGS. 1 to 14. Thus, the guide or guides can be made of NITINOL (Trademark) or any other suitable material which can be readily flexed and/or otherwise deformed but which exhibits a sufficient tendency to reassume a particular shape. All that counts is to ensure that the loop 7a and/or 7a' can be readily retracted into the single lumen or into the respective lumen of the tube 29 and that the exposed loop 7a and/or 7a' will move into a plane making a desired angle with the distal end of the tube 29 (if the guide 7 and/or 7' is provided with a resiliently deformable section 14 of the type shown in FIG. 18a) as soon as the loop 7a or 7a' is no longer confined in the distal end of the tube 29. Ready deformability of the loop 7a and/or 7a' is of particular importance when the endoscope 1A is utilized to illuminate and image selected portions of surfaces bounding the chambers in a heart 5. Thus, the loop 7a and 7a' can change its shape, when the endoscope 1A is in actual user in order to account for pulsatory movements of the heart and the resulting movements of the walls 28, 28a relative to each other.

An important advantage of the endoscope 1A which is shown in FIG. 21 is that the two loops 7a and 7a' even more reliably support the distal end of the tube 29 and the balloon 25 in a desired position relative to the respective walls 27 and 27a of the heart 5. The resiliently deformable sections (corresponding to the section 14 shown in FIG. 18a) of the guides 7 and 7' are selected in such a way that the plane of the loop 7a is inclined relative to the plane of the loop 7a', i.e., the planes of the loops 7a and 7a' make different angles with the longitudinal axis of the distal end of the tube 29. The illustrated angles for the planes of the loops 7a and 7a' are selected in such a way that the loop 7a' abuts the lowermost portion of the wall 27 within the chamber 28 and that the loop 7a engages a selected portion of the left-hand surface of the wall 27a in the chamber 28. At the same time, the guide 7 (not specifically shown in FIG. 21) and its loop 7a cooperate to maintain the distal end of the sheath 2 in an optimum position so that the inflated balloon 25 maintains the distal ends 24 of the conductors 23 in desired positions relative to the adjacent surface of the wall 27a. The mechanical support including the loops 7a and 7a' of FIG. 21 even more reliably ensures that the inflated balloon can expel blood from the region adjacent the distal ends 24 of the conductors 23 for as long as is necessary to complete the illumination and imaging of the adjacent portion of the left-hand surface of the wall 27a. The same applies for any other selected position of the balloon 25.

FIG. 21 also shows that the loops 7a and 7a' extend from the same side of the distal end portion of the tube 29, i.e., from the wall 27 toward the wall 27a. However, it is equally within the purview of the invention to design the distal end of the tube 29 in such a way that the loops 7a and 7a' are disposed in or close to a common plane but extend in different directions from the respective outlets of the tube 29 or that the loops extend in different directions and are located in different planes.

FIG. 21 further shows that the sheath 2 and the balloon 25 are slidable along a further guide having a follower 17 which can be caused to track the loop 7a. Of course, it is equally within the purview of the invention to install the sheath 2 in such a way that its distal end directly surrounds and is movable along the loop 7a or along the loop 7a'. Still further, it is possible to employ a fourth guide which corresponds to the guide including the follower 17 of FIG. 21 and to provide such fourth guide with a follower which is slidable along the loop 7a'. The fourth guide can be installed in such a way that its distal end can be expelled from the tube 29 by way of the outlet 31 (or through a separate outlet) when the loop 7a' is exposed and the sheath 2 (with the ballon 25) or a second sheet is to be moved along the exposed distal end of the fourth guide toward or away from a selected portion of the loop 7a'. Each follower 17 can constitute a hook, an eyelet, a sleeve or an analogous device which can be caused to slide along the loop 7a or 7a'.

Still further, the number of loops (and of the corresponding guides) can be increased to three or even more, as long as the diameter of the tube 29 remains within acceptable limits.

The follower 17 of FIG. 21 can be shifted along the loop 7a by a displacing element corresponding to the displacing element 30 shown in FIG. 22. The displacing element 30 can be moved axially by a handle (not shown) to move along the guide 7' (and its loop 7a' which is not shown in FIG. 22) and to displace the follower of the aforementioned fourth guide along the loop 7a'. The handle for the proximal end of the guide 7' of FIG. 22 is shown at 10. The displacing element 30 can be made of convoluted wire and can slide along the guide 7' in a manner analogous to that described in connection with the convoluted conductor assembly 4 and the guide 7 and loop 7a of FIG. 4.

The handle 2A at the proximal end of the sheath 2 can be used to strip the sheath off the guide 7 of FIG. 22 (upon detachment of the handle 107 from the proximal end of the guide 7) so that the sheath 2 can be replaced by a sheath carrying a different balloon or two or more balloons, or that the sheath 2 can be slipped onto the guide 7' (for movement along the loop 7a') or another guide.

An important advantage of the improved endoscope 1A is that that the balloon 25 (or each of two or more balloons, if necessary) forms part of the endoscope so that it need not be introduced into and withdrawn from a heart chamber or another internal space of a body organ by resorting to a discrete catheter. Furthermore, the balloon does not appreciably obstruct the flow of a body fluid in or into and from an internal space of a body organ when the improved endoscope is in actual use. This holds true for each situation when the balloon 25 is deflated as well as in every case when the balloon is inflated and thus ensures that the utilization of the endoscope 1A does not harm the patient while simultaneously ensuring a superior illumination and imaging of selected portions of surfaces bounding the internal spaces of body organs.

The provision of mechanical supporting means or frame (such as the loop 7a and/or 7a') for that portion of the sheath 2 which carries the balloon 6 constitutes an optional but highly desirable and advantageous feature of the improved endoscope. Such mechanical supporting means is particularly desirable and advantageous when the cross-sectional area of the space (e.g., the passage in an aorta or another large blood vessel or a chamber in a human or other animal heart) is very large so that it is desirable to undertake additional steps which ensure accurate positioning of a relatively small balloon in a selected portion of the passage in such a way that the properly inserted and expanded balloon cannot interfere (or cannot appreciably interfere) with the flow of blood or another body fluid and/or with pulsating or other necessary movements of a body organ, e.g., those movements which are attributable to the normal function of a heart and/or to respiration of the patient.

The balloon 6 constitutes a small but highly reliable enclosure for those portions of the conductors 23 which must remain exposed in order to ensure adequate illumination and adequate imaging of selected portions of surfaces bounding heart chambers, passages of large blood vessels or other spaces in body organs.

The dimensions of the mechanical support or frame can be varied in a simple and reliable manner, e.g., by increasing the size of the loop 7a' and/or 7a so that one and the same endoscope can be put to use under a wide range of different circumstances. The constituent or constituents of the mechanical support (such as the one including the loops 7a and 7a' shown in FIG. 21) occupy a minimal amount of space so that such mechanical support does not and cannot interfere with the flow of a body fluid and or with (respiratory and/or pulsating) movements of a body organ which is being inspected and imaged by the improved endoscope.

If the person in charge wishes to change the position of the balloon, the balloon can remain inflated as long as the dimensions of the support or frame are reduced sufficiently to ensure a predictable and atraumatic shifting of the (inflated, partially inflated or deflated) balloon to a different position.

The versatility of the improved endoscope can be selected practically at will. Thus, the balloon 25 can be mounted for movement along the loop 7a, along the loop 7a', along the guide for the sheath 2 which is shown in FIG. 21 and includes the follower 17, along one or more additional loops as well as with the distal end of the tube 29. The size of each loop is preferably variable, and such variations are or can be selected in such a way that the size is variable between an infinite number of different sizes. This ensures that the selected size of a loop is best suited for retention of the balloon 25 (or of one or more balloons) in an optimum position (or in optimum positions) relative to the adjacent surface in an internal space of a body organ.

The movability of distal ends 24 relative to the balloon 25 also constitutes an optional and desirable feature of the improved endoscope. For example, the distal ends 24 can be moved relative to the inflated balloon 25 so as to actually abut the internal surface of the balloon. Since the external surface of the balloon bears against the selected portion of the surface in an internal chamber of a body organ, the fluid (such as a liquid) which is selected to inflate the balloon cannot interfere with the transmission of radiation from one or more conductors 23 against the adjacent surface in an internal space and, at the same time, the expanded ballon expels blood or another body fluid from the region between the external surface of the inflated balloon and the adjacent portion of the internal surface of the body organ.

The illumination and imaging of an internal surface can be carried out in accordance with a preselected pattern. For example, and referring again to FIG. 16, the balloon 25 can be caused to advance the distal ends 24 of the conductors 23 along an endless path (along the loop 7a) while the axial position of the tube 29 remains unchanged. The axial position of the tube 29 is thereupon changed and the ballon 25 is again caused to move along the loop 7a, and so forth until the inspection of a selected portion of the surface bounding the chamber 28 in the heart 5 of FIG. 16 is completed.

The image or images which are furnished by certain conductors 23 can be inspected by the person in charge as the examination of the surface surrounding the cavity, the chamber, the passage or another internal space of a body organ progresses, or such images can be recorded in a manner not forming part of the present invention.

The preceding passages of this specification refer primarily to the heart and to the blood vessels of a patient who or which is being examined by resorting to the improved endoscope 1A. However, such instrument can be utilized with equal or similar advantage for the examination of the stomachs kidneys, liver, gallbladder, oesophagus and certain other organs of a human or other animal body.

The fluid which is used to inflate the balloon 25 can be any fluid (such as a liquid) which does not interfere with the transmission of radiation from the distal ends 24 of certain conductors 23 against the adjacent portion of a surface bounding an internal space and which does not interfere with the transmission of images from the illuminated portion of the surface into the distal ends of certain other conductors.

Without further analysis, the foregoing will so fully reveal the gist of the present invention that others can, by applying current knowledge, readily adapt it for various applications without omitting features that, from the standpoint of prior art, fairly constitute essential characteristics of the generic and specific aspects of the above outlined contribution to the art and, therefore, such adaptations should and are intended to be comprehended within the meaning and range of equivalence of the appended claims.

What is claimed is:

1. An endoscope comprising an elongated flexible sheath having a distal end insertable into an internal space of a body organ and a proximal end; a plurality of elongated flexible radiation- and and image-transmitting conductors surrounded by and extending longitudinally of said sheath and having exposed distal ends at the distal end of said sheath to direct radiation against and to transmit images of a surface bounding the internal space of the body organ receiving the distal end of said sheath; at least one inflatable and deflatable balloon surrounding the distal ends of said conductors; means for inflating and deflating said at least one balloon, including means for establishing for the flow of a fluid into and from said at least one balloon a path extending longitudinally of said sheath; an elongated flexible guide extending longitudinally of said sheath and including an elongated loop disposed at the distal end of said sheath and supporting said at least one balloon and the distal ends of said conductors for movement longitudinally of said loop; and means for moving said at least one balloon and the distal ends of said conductors along said loop.

2. The endoscope of claim 1, further comprising means for moving said guide relative to said sheath to thus vary the size of said loop.

3. The endoscope of claim 1, wherein said guide includes a strand having a distal portion connected with said loop and being inclined relative to a plane including said loop upon introduction of said loop into the internal space of a body organ.

4. The endoscope of claim 1, wherein said means for moving said balloon along said loop includes a tubular member having a follower tracking said loop and being movable along said loop to thereby shift said at least one balloon along said loop.

5. The endoscope of claim 1, wherein said loop includes a first end portion affixed to a distal end of an elongated flexible tube surrounding an intermediate portion of said sheath and a second end portion, said guide further including an elongated strand connected with the second end portion of said loop and extending through said tube from said distal end to a proximal end of the tube, said sheath and said at least one balloon being movable along and all the way to the first end portion of said loop.

6. An endoscope comprising an elongated flexible sheath having a distal end insertable into an internal space of a body organ and a proximal end; a plurality of elongated flexible radiation- and image-transmitting conductors surrounded by and extending longitudinally of said sheath and having exposed distal ends at the distal end of said sheath to direct radiation against and to transmit images of a surface bounding the internal space of the body organ receiving the distal end of said sheath; at least one inflatable and deflatable balloon surrounding the distal ends of said conductors; means for inflating and deflating said at least one balloon, including means for establishing for the flow of a fluid into and from said at least one balloon a path extending longitudinally of said sheath; an elongated flexible tube surrounding an intermediate portion of said sheath and having a distal end and a proximal end; and a guide including an elongated loop at the distal end of said tube, said at least one balloon and said distal ends of said conductors being guided by and being movable along said loop in the longitudinal direction of the loop and said loop exhibiting a tendency to move into a plane making a predetermined angle with the distal end of said tube.

7. An endoscope comprising an elongated flexible sheath having a distal end insertable into an internal space of a body organ and a proximal end; a plurality of elongated flexible radiation- and image-transmitting conductors surrounded by and extending longitudinally of said sheath and having exposed distal ends at the distal end of said sheath to direct radiation against and to transmit images of a surface bounding the internal space of the body organ receiving the distal end of said sheath; at least one inflatable and deflatable balloon surrounding the distal ends of said conductors; means for inflating and deflating said at least one balloon, including means for establishing for the flow of a fluid into and from said at least one balloon a path extending longitudinally of said sheath; an elongated flexible tube surrounding an intermediate portion of said sheath; and a guide for said at least one balloon, said guide including a loop having a first end portion affixed to a distal end of said tube and a second end portion extending into the distal end of said tube substantially diametrically opposite said first end portion with reference to a longitudinal axis of said distal end of said tube.

8. An endoscope comprising an elongated flexible sheath having a distal end insertable into an internal space of a body organ and a proximal end; a plurality of elongated flexible radiation- and image-transmitting conductors surrounded by and extending longitudinally of said sheath and having exposed distal ends at the distal end of said sheath to direct radiation against and to transmit images of a surface bounding the internal space of the body organ receiving the distal end of said sheath; at least one inflatable and deflatable balloon surrounding the distal ends of said conductors; means for inflating and deflating said balloon, including means for establishing for the flow of a fluid into and from said at least one balloon a path extending longitudinally of said sheath; and a three-dimensional frame arranged to support said at least one balloon in the internal space of the body organ, said frame including a plurality of resiliently deformable loops including a loop engageable with the surface bounding the internal space of the body organ receiving said frame and said at least one balloon.

9. The endoscope of claim 8, wherein said loops are disposed in planes which are inclined relative to each other.

10. The endoscope of claim 8, wherein said frame further comprises an elongated flexible tube surrounding an intermediate portion of said sheath and having a distal end adjacent and supporting said loops.

11. The endoscope of claim 8, wherein said distal end of said sheath and said at least one balloon are slidable along at least one of said loops.

12. The endoscope of claim 8, wherein said frame further comprises an elongated flexible tube surrounding an intermediate portion of said sheath and having a distal end adjacent said loops, a first flexible guide extending longitudinally of said tube and connected with one of said loops, and a second elongated guide extending longitudinally of said tube and connected with another of said loops, at least one of said guides having a portion confined in and movable longitudinally of said tube.

13. An endoscope comprising an elongated flexible sheath having a distal end insertable into an internal space of a body organ and a proximal end; a plurality of elongated flexible radiation- and image-transmitting conductors surrounded by and extending longitudinally of said sheath and having exposed distal ends at the distal end of said sheath to direct radiation against and to transmit images of a surface bounding the internal space of the body organ receiving the distal end of said sheath; at least one inflatable and deflatable balloon surrounding the distal ends of said conductors; means for inflating and deflating said at least one balloon, including means for establishing for the flow of a fluid into and from said at least one balloon a path extending longitudinally of said sheath; and a frame for said at least one balloon in the internal space of the body organ, said frame including an elongated flexible tube having at least one longitudinally extending lumen, and guide means for said at least one balloon and the distal ends of said conductors, said guide means including at least one loop provided at a distal end of said tube and said at least one lumen having an open end in said distal end of said tube, said at least one loop and said distal ends of said conductors and said at least one balloon being retractible into said at least one lumen by way of said open end, said at least one balloon and the distal ends of said conductors being movable along said at least one loop in the non-retracted position of said at least one loop.

14. An endoscope comprising an elongated flexible sheath having a distal end insertable into an internal space of a body organ and a proximal end; a plurality of elongated flexible radiation- and image-transmitting conductors surrounded by and extending longitudinally of said sheath and having exposed distal ends at the distal end of said sheath to direct radiation against and to transmit images of a surface bounding the internal space of the body organ receiving the distal end of said sheath; at least one inflatable and deflatable balloon surrounding the distal ends of said conductors, said at least one balloon including a deformable wall having a radiation transmitting portion which is adjacent the distal ends of said conductors and is closely adjacent a portion of the surface bounding the internal space in the inflated condition of said at least one balloon; means for inflating and deflating said at least one balloon, including means for establishing for the flow of a fluid flowing into and from said at least one balloon a path extending longitudinally of said sheath; and a mechanical support including means for urging said portion of the deformable wall of the at least one balloon against said portion of the surface bounding the internal space in the inflated condition of said at least one balloon, said means for urging including an elongated flexible tube surrounding said conductors at least between the proximal and distal ends of the conductors and including a distal end at the distal ends of said conductors, and at least one guide including an elongated portion confined in said tube and a distal end portion extendable from the distal end of said tube to engage the surface in the internal space of the body organ adjacent said at least one balloon, said means for urging further comprising means for moving said elongated portion of said at least one guide longitudinally of said tube to thus vary the size of the distal end portion of said at least one guide, said distal end portion of said at least one guide including a loop extendible from the distal end of said tube to engage a portion of the surface bounding the internal space of the body organ.

15. The endoscope of claim 14, wherein said means for establishing said path includes a lumen in said sheath.

16. The endoscope of claim 14, wherein said at least one guide includes at least one metallic wire.

17. The endoscope of claim 14, wherein said at least one guide includes at least one plastic wire.

18. The endoscope of claim 14, wherein said tube surrounds a portion of said sheath.

19. The endoscope of claim 14, wherein said means for moving includes means for shifting said at least one guide relative to said tube between a plurality of different positions to thereby select any one of a plurality of different sizes of said loop.

20. The endoscope of claim 14, further comprising means for retracting said at least one balloon into and for expelling said at least one balloon from the distal end of said tube.

21. The endoscope of claim 14, wherein said at least one balloon has an internal channel and said conductors include portions extending into and being movable lengthwise in said channel.

22. The endoscope of claim 21, wherein said means for moving includes said sheath.

23. The endoscope of claim 14, wherein said at least one guide movably supports said at least one balloon and the distal ends of said conductors, said guide including at least one resiliently deformable wire.

24. The endoscope of claim 23, wherein said at least one wire consists of a metallic material.

25. The endoscope of claim 23, wherein said at least one wire consists of a plastic material.

26. An endoscope comprising an elongated flexible sheath having a distal end insertable into an internal space of a body organ and a proximal end; a plurality of elongated flexible radiation- and image-transmitting conductors surrounded by and extending longitudinally of said sheath and having exposed distal ends at the distal end of said sheath to direct radiation against and to transmit images of a surface bounding the internal space of the body organ receiving the distal end of said sheath; at least one inflatable and deflatable balloon surrounding the distal ends of said conductors, said at least one balloon including a deformable wall having a radiation transmitting portion which is adjacent the distal ends of said conductors and is closely adjacent a portion of the surface bounding the internal space in the inflated condition of said at least one balloon; means for inflating and deflating said at least one balloon, including means for establishing for the flow of a fluid into and from said at least one balloon a path extending longitudinally of said sheath; a mechanical support including means for urging said portion of the deformable wall of the at least one balloon against said portion of the surface bounding the internal space in the inflated condition of said at least one balloon, said means for urging including an elongated flexible tube surrounding said conductors at least between the proximal and distal ends of the conductors and including a distal end at the distal ends of said conductors, and at least one guide including an elongated portion confined in said tube and a distal end portion extendable from the distal end of said tube to engage the surface in the internal space of the body organ adjacent said at least one balloon; and means for retracting said at least one balloon into and for expelling said at least one balloon from the distal end of said tube.

* * * * *